United States Patent [19]
McDonald et al.

[11] Patent Number: 5,837,283
[45] Date of Patent: Nov. 17, 1998

[54] CATIONIC LIPID COMPOSITIONS TARGETING ANGIOGENIC ENDOTHELIAL CELLS

[75] Inventors: Donald M. McDonald, San Francisco; John McLean, Redwood City; O. Gavin Thurston; Peter Baluk, both of San Francisco, all of Calif.

[73] Assignee: The Regents of the University of California, Oakland, Calif.

[21] Appl. No.: 820,337

[22] Filed: Mar. 12, 1997

[51] Int. Cl.$^6$ .................................................. A61K 9/127
[52] U.S. Cl. .............................................. 424/450; 935/54
[58] Field of Search ..................................... 424/450, 460; 530/316, 388.7, 380, 381, 382; 514/8; 935/54; 436/829

[56] References Cited

U.S. PATENT DOCUMENTS

| | | |
|---|---|---|
| 4,394,448 | 7/1983 | Szoka, Jr. et al. . |
| 4,897,355 | 1/1990 | Eppstein et al. . |
| 5,092,885 | 3/1992 | Yamada et al. . |
| 5,110,730 | 5/1992 | Edington et al. ............... 435/69.6 |
| 5,192,744 | 3/1993 | Bouck et al. . |
| 5,202,352 | 4/1993 | Okada et al. . |
| 5,328,470 | 7/1994 | Nabel et al. . |
| 5,512,294 | 4/1996 | Li et al. ............................ 424/450 |

FOREIGN PATENT DOCUMENTS

| | | |
|---|---|---|
| 91/06309 | 5/1991 | WIPO . |
| 93/12240 | 6/1993 | WIPO . |
| 93/12756 | 7/1993 | WIPO . |
| 93/24640 | 12/1993 | WIPO . |
| 93/25673 | 12/1993 | WIPO . |
| 95/25543 | 9/1995 | WIPO . |

OTHER PUBLICATIONS

Brigham, K.L., et al., (1989) "Expression of a Prokaryotic Gene in Cultured Lung Endothelial Cells after Lipofection with a Plasmid Vector," *Am. J. Respir. Cell Mol. Biol.* 1: 95–100.

Brigham, K.L., et al. (1989) "Rapid Communication: In vivo Transfection of Murine Lungs with a Functioning Prokaryotic Gene Using a Liposome Vehicle," from the Center for Lung Research, Dept. of Med. Path. and Molecular Phys. and Biophys., Vanderbilt U. School of Med., Nashville, Tenn. pp. 278–284.

Burrows, F.J., et al., (1993) "Eradication of large solid tumors in mice with an immunotoxin directed against tumor vasculature," *Proc. Natl. Acad. Sci. USA* 90: 8996–9000.

Felgner, P.L., et al., (1991) "Gene Therapeutics" *Nature* 349: 351–352.

Felgner, P.L., et al., (1987) "Lipofection: A highly efficient, lipid–mediated DNA–transfection procedure," *Proc. Natl. Acad. Sci. USA* 84: 7413–7417.

Folkman, J. et al., (1989) "Induction of angiogenesis during the transition from hyperplasia to neoplasia," *Nature* 339: 58–61.

Folkman, J., et al., (1987) "Angiogenic Factors," *Science* 235:442–447.

Gao, X., et al., (1995) "Cationic liposome–mediated gene transfer," *Gene Therapy* 2: 710–722.

Hanahan, D., et al., (1996) "Patterns and Emerging Mechanisms of the Angiogenic Switch during Tumorigenesis," *Cell* 86: 353–364.

Huang, X., et al., (1997) "Tumor Infarction in Mice by Antibody–Directed Targeting of Tissue Factor to Tumor Vasculature," *Science* 275: 547–550.

(List continued on next page.)

*Primary Examiner*—Gollamudi S. Kishore
*Attorney, Agent, or Firm*—Bozicevic & Reed LLP; Karl Bozicevic

[57] ABSTRACT

Angiogenic endothelial cells are selectively targeted with lipid/DNA complexes or cationic liposomes containing a substance which affects the targeted cells by inhibiting or promoting their growth. A site of angiogenesis can be precisely located by administering cationic liposomes containing a detectable label. The complexes may comprise nucleotide constructs which are comprised of promoters which are selectively and exclusively activated in the environment of an angiogenic endothelial cell.

13 Claims, 13 Drawing Sheets

OTHER PUBLICATIONS

Lasic, D.D., (1993) *Liposomes: From Physics to Applications,* Elsevier, N.Y., 265–493.

Xu, M., et al., "Parenteral Gene Therapy with p53 Inhibits Human Breast Tumors in Vivo Through a Bystander Mechanism Without Evidence of Toxicity," *Human Gene Therapy* 8:177–185.

CATIONIC LIPID COMPOSITIONS TARGETING ANGIOGENIC ENDOTHELIAL CELLS

BACKGROUND OF THE INVENTION

The present invention can be applied to the treatment and diagnosis of a variety of different diseases and abnormalities. Although the present invention is not limited to such, it can be used in the treatment of cancer, wound healing, and a variety of chronic inflammatory diseases. In general, each is presently treated directly by physical means such as surgical removal of cancerous tissue, suturing of wounds and surgical removal of inflamed joints. Further, each can be treated by chemical means. Chemotherapy is applied to cancers, growth hormones are applied to wound healing and anti-inflammatory drugs are applied to treating chronic inflammatory conditions. These, and related treatments are directed, in general, to treating the cancerous, injured, or inflamed tissue directly. In order to provide an understanding on how the present invention departs from conventional treatment modalities a brief and general description of current treatment technologies in these areas is provided.

CANCER TREATMENTS

The term "cancer" encompasses a spectrum of diseases that vary in treatment, prognosis, and curability. The approach to diagnosis and treatment depends on the site of tumor origin, the extent of spread, sites of involvement, the physiologic state of the patient, and prognosis. Once diagnosed, the tumor is usually "staged," a process which involves using the techniques of surgery, physical examination, histopathology, imaging, and laboratory evaluation to define the extent of disease and to divide the cancer patient population into groups in order of decreasing probability of cure. Such systems are used both to plan treatment and determine the prognoses for the patient (Stockdale, F., 1996, "Principles of Cancer Patient Management," In: Scientific American Medicine, vol. 3, Dale, D. C., and Federman, D. D. (eds.), Scientific American Press, New York). The type or stage of the cancer can determine which of the three general types of treatment will be used: surgery, radiation therapy, and chemotherapy. An aggressive, combined modality treatment plan can also be chosen. To this end, surgery can be used to remove the primary tumor, and the remaining cells are treated with radiation therapy or chemotherapy (Rosenberg, S. A., 1985, "Combined-modality therapy of cancer: what is it and when does it work?" *New Engl. J. Med.* 312:1512–14).

Surgery plays the central role in the diagnosis and treatment of cancer. In general, a surgical approach is required for biopsy, and surgery can be the definitive treatment for most patients with cancer. Surgery is also used to reduce tumor mass, to resect metastases, to resolve medical emergencies, to palliate and rehabilitate. Although the primary surgical technique for cancer treatment has involved the development of an operative field where tumors are resected under direct visualization, current techniques allow for some resections to be performed by endoscopic means. A primary concern in the treatment of cancer is the consideration of operative risk (Stockdale, F., supra).

Radiation therapy plays an important role in both the primary and palliative treatment of cancer. Both teletherapy (megavoltage radiation therapy) and brachytherapy (interstitial and intracavity radiation) are in common use. Electromagnetic radiation in the form of x-rays is most commonly used in teletherapy to treat common malignant tumors, while gamma rays, a form of electromagnetic radiation similar to x-rays but emitted by radioactive isotopes of radium, cobalt, and other elements, are also used. Radiation therapy transfers energy to tissues as discrete packets of energy, called photons, that damage both malignant and normal tissues by producing ionization within cells. The target for the ions is most commonly the DNA; radiation therapy exploits the fact that the radiation damage is not uniform between malignant and non-malignant tissues—rapidly dividing cells are more sensitive to DNA damage than quiescent cells (Pass, H. I., 1993, "Photodynamic therapy in oncology: mechanisms and clinical use," J. Natl. Cancer Instit. 85:443–56.) Radiation therapy is associated with unique benefits as well as important toxicities. Radiation is preferred in certain anatomic areas, (e.g., the mediastinum), where radiation may be the only feasible local method of treatment, and radiation may also be the only feasible local modality if tumor involvement is extensive. Radiation may also be used when the patient finds surgery unacceptable, or when the patient's medical condition prohibits a surgical procedure. Radiation treatment involves tissue damage which can lead to early and late radiation effects. The early effects (acute toxicity of radiation therapy) include erythema of the skin, desquamation, esophagitis, nausea, alopecia, and mylosupression, while the late effects include tissue necrosis and fibrosis, and usually determine the limiting toxicity of radiation therapy (Stockdale, F., supra).

Nearly all chemotherapeutic agents currently in use interfere with DNA synthesis, with the provision of precursors for DNA and RNA synthesis, or with mitosis, and thus target proliferating cells (Stockdale, F., "Cancer growth and chemotherapy," supra). Animal tumor investigation and human clinical trials have shown that drug combinations produce higher rates of objective response and longer survival than single agents (Frei, E. III, 1972, "Combination cancer therapy: presidential address," *Cancer Res.* 32:2593–2607). Combination drug therapy uses the different mechanisms of action and cytotoxic potentials of multiple drugs, including the alkylating agents, antimetabolites, and antibiotics (Devita, V. T., et al., 1975, "Combination versus single agent chemotherapy: a review of the basis for selection of drug treatment of cancer," Cancer 35:98–110). The physiologic condition of the patient, the growth characteristics of the tumor, the heterogeneity of the tumor cell population, and the multidrug resistance status of the tumor influence the efficacy of chemotherapy. Generally, chemotherapy is not targeted (although these techniques are being developed, e.g. Pastan, I. et al., 1986, "Immunotoxins," *Cell* 47:641–648), and side effects such as bone marrow depression, gastroenteritis, nausea, alopecia, liver or lung damage, or sterility can result.

WOUND HEALING

Wound healing is a complex and protracted process of tissue repair and remodeling involving many different cell types which requires a finely tuned control of various biochemical reaction cascades to balance the regenerative processes. Wound healing is generally divided into three phases: inflammation, proliferation, and maturation (Waldorf, H., and Fewkes, J., 1995, "Wound Healing," Adv. Dermatol. 10:77–96). The process comprises the migration of different cell types into the wound region, growth stimulation of epithelial cells and fibroblasts, formation of new blood vessels, and the generation of extracellular matrix. The correct functioning of these processes depends on the biological activation of various cytokines (Bennett, N. T., and Schultz, G. S., 1993, "Growth factors and wound healing: biochemical properties of growth factors and their receptors," Am. J. Surg. 165:728–37). Nutrition, the immune system, oxygen, blood volume, infection, immunosuppression, and a decrease in red blood cells are all influential factors in wound healing (Witney, J. D., 1989, "Physiological Effects of tissue oxygenation on wound healing," Heart Lung 18: 466–474).

The quality as well as the rate of wound healing is usually dependent on the type and extent of the original injury. Three general types of process are used to treat wounds, each of which is directed to healing the damaged tissue. Closure of wounds is most commonly accomplished by suturing, although tapes, stapling or electrocautery can also be used (Wheeless, C. R., 1996, Wheeless' *Textbook of Orthaedics*) (Garrett, W. E., et al., 1984, *J. Hand. Surg.* 9(5):683–92). Skin tapes and various sutures each exhibit certain benefits and disadvantages in primary closure of wounds. Skin tapes cause less inflammatory reaction but fail to close the subepithelial wound spaces, while the inflammatory reaction and subsequent scarring caused by various sutures depends upon the size of the suture needle, the diameter of the suture material, and whether it is a monofilament or woven suture (Simpson, W. R., 1977, "Physiological principles of therapy in head and neck cutaneous wounds," *Laryngoscope* 87: 792–816).

In a wound, the size of an inoculum of microorganisms, the virulence of the organisms, and host antimicrobial defense mechanisms determine if an infection will develop. Thus, antibiotics can also be of therapeutic value in the treatment of wounds (Edlich, R. F., et al., 1986, "Antimicrobial treatment of minor soft tissue lacerations: a critical review," *Emergency Medical Clinics of North America* 4(3) :561–80). The pharmacological action of each antibiotic must be understood in order to choose the proper antibiotic, its route of administration, and to avoid side effects (Simpson, W. R., supra). Recent results suggest that antibiotic therapy allows cell proliferation and differentiation to proceed more rapidly and thus may be helpful in augmenting wound repair (Barrow, R. E., et al., 1994, "Efficacy of cefazolin in promoting ovine tracheal epithelial repair," *Respiration* 61:231–5; Maeder, K., et al., 1993, "Methicillin-resistant *Staphylococcus aureus* (MRSA) colonization in patients with spinal cord injury," *Paraplegia* 31: 639–44). Proteolytic enzymes have also been used as adjuncts to antibiotic treatment of contaminated wounds (Rodeheaver, G. T., et al., 1978, "Mechanisms by which proteolytic enzymes prolong the golden period of antibiotic action," *Am. J. Surg.* 136(3) :379–82).

The topical administration of various cytokines, including bFGF, EGF, PDGF, and TGF-beta, either alone or in combination, may considerably accelerate wound healing (Moulin, V., 1995, "Growth factors in skin wound healing," *Eur. J. Cell. Biol.* 68:1–7). Growth factors attract cells into the wound, stimulate their proliferation, and have profound influence on extracellular matrix deposition. Since developing the ability to mass-produce these cytokines by recombinant techniques, many studies have demonstrated that growth factors can augment all aspects of tissue repair in normal and impaired healing models (e.g., Schultz, G. S., et al., 1987, "Epithelial wound healing enhanced by transforming growth factor-alpha and vaccinia growth factor," *Science* 235: 350–2; Deuel, T. F., et al., 1991, "Growth factor and wound healing: platelet derived growth factor as a model cytokine," *Annu. Rev. Med.* 42: 567–84). Although preliminary clinical trials have shown that growth factor treatment has occasionally led to statistically significant improvements in tissue repair, it is not clear that these results are clinically significant, and it has been suggested that new clinical trials must focus on targeting growth factors for specific types of impaired healing (Greenhalgh, D. G., 1996, "The role of growth factors in wound healing," *J. Trauma* 41:159–67).

CHRONIC INFLAMMATION

Natural, humoral, and cellular immune mechanisms have all been implicated in the pathogenesis of chronic inflammatory diseases (Seymour, G. J., et al., 1979, "The immunopathogenesis of progressive chronic inflammatory periodontal disease, 1979, "*J. Oral Pathol.* 8:249–65). Autoimmune diseases result from abnormalities in lymphocyte function. Abnormalities in T cell function can be responsible for disease through cell-mediated immunity, and the activity of helper T cells in the production of antibodies may contribute to autoantibody formation. The central role of helper T cells in autoimmune disease is supported by the association of many of these diseases with certain HLA molecules. The failure of one or more steps in the maintenance of tolerance could result in autoimmunity (Robinson, D. R., 1996, "Immunologic Tolerance and Autoimmunity," in: Scientific American Medicine, Vol. 2, Section VI, Scientific American Press, New York, p.1–11).

Several types of treatment are used in autoimmune disease, all of which are directed at lessening the immune response in the affected tissue. For example, treatment for rheumatoid arthritis, an autoimmune disease, can utilize anti-inflammatory agents such as nonsteroidal anti-inflammatory agents (NSAIDs) or glucocorticosteroids, remission inducing agents such as gold salts, and/or immunosuppressive drugs such as cyclophosphamide. Orthopedic surgery can also be used to replace joints damaged during the inflammatory process (see Gilliland, B. C., and Mannik, M., 1983, "Rheumatoid Arthritis" In: *Harrison's Principles of Internal Medicine*, McGraw Hill, New York, P. 1977–1984). Recent work has suggested the possibilities of new treatments, also directed to the affected tissue, such as the use of TNF alpha in the treatment of rheumatoid arthritis (Brennan, F. M., et al., 1995, "Cytokine expression in chronic inflammatory disease," *Br. Med. Bull.* 51:368–384).

Allergy refers to a condition in which the immune response to environmental antigens causes tissue inflammation and organ disfunction. As in the autoimmune diseases, the data suggest an interaction of several components of the immune system in allergic diseases. The diversity of expression of allergic diseases arises from different immunologic effector mechanisms, which evoke specific patterns of tissue injury (Beer, D. J. et al., 1996. "Allergy," In: *Scientific American Medicine,* Vol. 2, Section VII, Scientific American Press, New York, P. 1–29). The clinical features of each allergic disease reflect the immunologically mediated inflammatory response in the affected organs or tissues (e.g. asthma reflects an inflammatory response in the lungs).

Several treatment strategies are used to treat the immune-mediated allergic diseases, all of which are directed at lessening the immune response in the inflamed tissue. For example, in the treatment of asthma, therapy can involve environmental control, pharmacotherapy, and allergin immunotherapy (Beer, D. J., et al., 1996, "Allergy," In: *Scientific American Medicine,* Vol. 2, Section VII, Scientific American Press, New York, P. 1–29). In the treatment of asthma, elimination of the causative agent is the most successful means of preventing the inflammation. However, this is often not possible, and thus several classes of drugs have been used. These include the methylxanthines (for bronchodilation), adrenergic stimulants (stimulation of β-adrenergic receptors, bronchodilators), glucocorticoids (lessen inflammation in the lung), chromones (downregulate mast cells, lessen inflammation in the lung), and anticholinergics (bronchodilators)( McFadden, E. R., Jr., and Austen, K. F., "Lung disease caused by immunologic and environmental injury," In: *Harrison's Principles of Internal Medicine,* McGraw Hill, New York, p. 1512–1519). Desensitization or immunotherapy with extracts of the suspected allergens has also been suggested in order to reduce inflammation in asthma (McFadden and Austen, op. cit.; Jacquemin, M. G., and Saint-Remy, J. M., 1995, "Specific down-regulation of anti-allergen IgE and IgG antibodies in humans associated with injections of allergen-specific antibody complexes," *Ther. Immunol.* 2:41–52).

CURRENT TREATMENTS-IMMUNOLOGY

The treatment regimes described above have had varying degrees of success. Because the success rate is far from perfect in many cases research continues to develop better treatments. One promising area of research relates to affecting the immune system. By the use of genetic engineering and/or chemical stimulation it is possible to modify and/or stimulate immune responses so that the body's own immune system treats the disease e.g., antibodies destroy cancer cells. This type of treatment departs from those described above in that it utilizes a biological process to fight a disease. However, the treatment is still a direct treatment meaning that the antibodies created directly attack the cancer cells.

The present invention can be utilized for treatments which involve a radical departure from normal treatments in that the present invention does not involve directly affecting the cancerous, damaged or inflamed cells.

Others have recognized that, at least theoretically, it is possible to treat cancer or inflammation associated with angiogenesis by inhibiting the angiogenesis. A typical example of the current thinking relating to such is discussed within PCT Publication WO 95/25543, published Sep. 28, 1995. This published application describes inhibiting angiogenesis by administering an antibody which binds to an antigen believed to be present on the surface of angiogenic endothelial cells. Specifically, the application describes administering an antibody which binds to $\alpha_v\beta_3$ which is a membrane receptor believed to mediate cell-cell and cell-extracellular matrix interactions referred to generally as cell adhesion events. By blocking this receptor the treatment hopes to inhibit angiogenesis and thereby treat cancer and inflammation.

SUMMARY OF THE INVENTION

A method of selectively delivering agents to angiogenic endothelial cells is disclosed. The method involves injecting, preferably into the circulatory system and more preferably intraarterially, cationic liposomes (or polynucleotide/lipid complexes) which comprise cationic lipids and a compound which promotes or inhibits angiogenesis and/or includes a detectable label. After administration, the cationic liposomes selectively associate with angiogenic endothelial cells meaning that they associate with angiogenic endothelial cells at a five fold or greater ratio (preferably ten fold or greater) than they associate with corresponding, quiescent endothelial cells not undergoing angiogenesis. When the liposomes (or polynucleotide/lipid complexes) associate with angiogenic endothelial cells, they are taken up by the endothelial cell and have their desired effect. The substance can destroy the endothelial cell, promote further angiogenesis, promote clotting and/or tag the endothelial cell so that it can be detected by an appropriate means. The substance which affects the angiogenic endothelial cell may be a nucleotide sequence such as DNA which encodes a protein, which when expressed, promotes or inhibits angiogenesis. The nucleotide sequence is preferably contained within a vector operably connected to a promoter which promoter is preferably only active in angiogenic endothelial cells or can be activated in those cells by the administration of a compound thereby making it possible to turn the gene on or off by activation of the promoter.

An object of the invention is to provide a method of selectively affecting angiogenic endothelial cells, thereby inhibiting or promoting angiogenesis.

Another object of the invention is to provide a method for diagnosing a site of angiogenesis by administering cationic liposomes containing a detectable label which liposomes are designed so as to selectively associate with angiogenic endothelial cells and to not associate with corresponding endothelial cells not undergoing angiogenesis.

Another object of the invention is to provide cationic liposomes which liposomes are comprised of cationic lipids and compounds which are specifically intended and designed to either inhibit or promote angiogenesis which compounds may be water soluble or readily dispersable in water or lipid compatible and incorporated in the lipid layers.

Another object of the invention is to provide a method of selectively affecting angiogenic endothelial cells in a manner which results in local intravascular blood clotting which hinders or completely blocks the flow of blood in a blood vessel.

Another object is to provide a method for analyzing angiogenic endothelial cells by labeling cells with a detectable label and thereby making it possible to separate the angiogenic endothelial cells away from surrounding cells for subsequent culturing and/or analysis.

Yet another object of the invention is to provide a method for destroying an unwanted tumor by delivering a toxic compound to angiogenic endothelial cells of the tumor, which compound destroys the angiogenic endothelial cells and, thereafter, destroys the tumor cells.

Another object of the invention is to provide a method for selectively affecting angiogenic endothelial cells by delivering a cationic lipid/DNA complex to angiogenic endothelial cells, wherein the DNA is attached to a promoter which is selectively activated within an environment which is preferably uniquely associated with angiogenic endothelial cells, i.e., the promoter is not activated in quiescent endothelial cells.

A feature of the invention is that the cationic liposomes of the invention selectively associate with angiogenic endothelial cells with a much higher preference (five-fold or greater and preferably ten-fold or greater) than they associate with corresponding endothelial cells not involved in angiogenesis.

An advantage of the invention is that the cationic liposomes of the invention can be used to precisely deliver small amounts of toxic compounds to endothelial cells which cells are affected in a manner (e.g., killed) such that the blood vessel is destroyed or rendered inoperative such as by a blood clot and the nutrient supply to the surrounding tissues (such as tumor cells) is cut off thereby destroying the tissue (e.g., destroying a solid tumor).

Another advantage of the invention is that the cationic liposomes of the invention can be used to inhibit angiogenesis associated with malignant or benign tumors associated with on-going angiogenesis.

Yet another advantage of the invention is that the cationic liposomes can be used to provide for site directed delivery of compounds which promote angiogenesis and thereby enhance wound healing.

An important feature of the invention is that several classes of diseases and/or abnormalities are treated without directly treating the tissue involved in the abnormality e.g., by inhibiting angiogenesis the blood supply to a tumor is cut off and the tumor is killed without directly treating the tumor cells in any manner.

These and other objects, advantages and features of the present invention will become apparent to those skilled in the art upon reading the disclosure provided here in connection with the attached figures.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

DETAILED DESCRIPTION OF PREFERRED EMBODIMENTS

Figure 1:
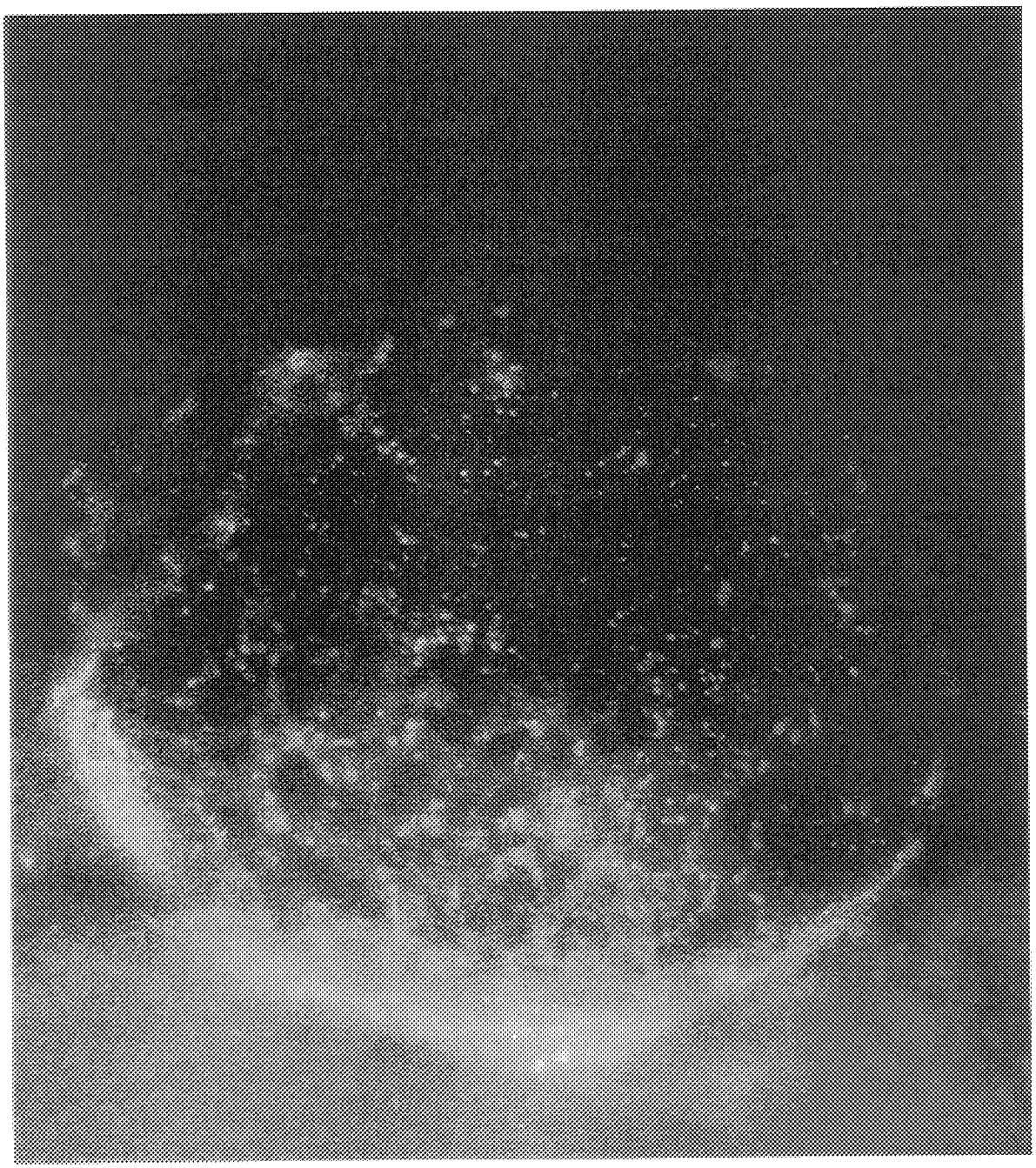
FIG. 1 is a fluorescence micrograph showing the uptake of red fluorescent CM-DiI-labeled DDAB:cholesterol-DNA complexes in angiogenic blood vessels of a follicle in a normal mouse ovary (Scale bar: 60 µm)

Before the present method of selectively affecting/labeling angiogenic endothelial cells and liposomes used in the method are described, it is to be understood that this invention is not limited to the particular liposomes, methods, or active substances described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and," and "the" include plural referents unless the contexts clearly dictates otherwise. Thus, for example, reference to "a liposome" includes mixtures and large numbers of such liposomes, reference to "an agent" includes large numbers of agents and mixtures thereof, and reference to "the method" includes one or more methods or steps of the type described herein.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

DEFINITIONS

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes:

(a) preventing the disease or symptom from occurring in a subject which may be predisposed to the disease or symptom but has not yet been diagnosed as having it;

(b) inhibiting the disease symptom, i.e., arresting its development; or (c) relieving the disease symptom, i.e., causing regression of the disease or symptom.

The term "angiogenesis" refers to a process of tissue vascularization that involves the development of new vessels. Angiogenesis occurs via one of three mechanisms: (1) neovascularization, where endothelial cells migrate out of pre-existing vessels beginning the formation of the new vessels; (2) vasculogenesis, where the vessels arise from precursor cells de novo; or (3) vascular expansion, where existing small vessels enlarge in diameter to form larger vessels (Blood, C. H. and Zetter, B. R., 1990, *Biochem. Biophys. Acta.* 1032:89–118).

Angiogenesis is an important process in normal processes of neonatal growth and in the female reproductive system during the corpus luteum growth cycle (see Moses, M. A., et al., 1990, Science 248: 1408–10). Under normal conditions, all processes involving the new formation or the remodeling of existing or new blood vessels is a self-limiting process, and the expansion of the specific cell types is controlled and concerted.

Angiogenesis is also involved in wound healing and in the pathogenesis of a large number of clinical diseases including tissue inflammation, arthritis, asthma, tumor growth, diabetic retinopathy, and other conditions. Clinical manifestations associated with angiogenesis are referred to as angiogenic diseases (Folkman, J. and Klagsbrun, M., 1987, *Science* 235: 442–7).

Many experiments have suggested that tissues can produce angiogenic factors which promote angiogenesis under conditions of poor blood supply during both normal and pathological conditions. These factors and compounds differ in cell specificity and in the mechanisms by which they induce the growth of new blood vessels. These factors function through a variety of mechanisms. For example, they may induce the migration and proliferation of endothelial cells or stimulate the production collagenase (see Klagsbrun, M, and D'Amore, P. A., 1991, "Regulators of angiogenesis," *Ann. Rev. Physiol.* 53:217–39). There are a number of bioassays which allow direct determination of angiogenic activities (Wilting, J., et al., 1991, "A modified chorioallantoic membrane (CAM) assay for qualitative and quantitative study of growth factors. Studies on the effects of carriers, PBS, angiogenin, and bFGF," *Anat. Embrol.* (Berl) 183:259–71).

It has been proposed that angiogenic inhibitors may be useful in the treatment of diseases. For example, interfering with angiogenesis may restrict tumor growth. Several means for inhibiting angiogenesis have been proposed including (1) inhibiting the release of angiogenic factors, (2) neutralizing angiogenic factors using such means as monoclonal antibodies, and (3) inhibiting endothelial cell responses (Folkman, J., et al, 1992, *Seminars in Cancer Biology* 3:89–96), through the use of anti-angiogenic factors, molecules known to inhibit angiogenesis. Several such endothelial cell inhibitors have been described such as collagenase inhibitor, basement membrane turnover inhibitors, angiostatic steroids, fungal-derived inhibitors, platelet factor 4, thrombospondin, arthritis drugs such as penicillamine, and alpha-interferon, among others (see Folknam, J., et al, 1992, *Seminars in Cancer Biology* 3:89–96; for examples see: Stepien, H., et al., 1996, "Inhibitory effects of fumagillin and its analogue TNP-470 on the function, morphology, and angiogenesis of an oestrogen-induced prolactinoma in Fischer 344 rats," *J. Endocrinol.* 150:99–106; Maione, T. E., et al., 1990, "Inhibition of angiogenesis by recombinant human platelet factor-4 and related peptides," *Science* 247: 77–9).

The term "endothelial cells" means those cells making up the endothelium, the monolayer of simple squamous cells which lines the inner surface of the circulatory system. These cells retain a capacity for cell division, although they proliferate very slowly under normal conditions, undergoing cell division perhaps only once a year. The proliferation of endothelial cells can be demonstrated by using [$^3$H] thymidine to label cells in the S phase. In normal vessels the proportion of endothelial cells that become labelled is especially high at branch points in arteries, where turbulence and wear seem to stimulate turnover. (Goss, R. J., 1978, *The Physiology of Growth*, Academic Press, New York, pp.120–137). Normal endothelial cells are quiescent i.e., are not dividing and as such are distinguishable from angiogenic endothelial cells as discussed below.

Endothelial cells also have the capacity to migrate, a process important in angiogenesis.

Endothelial cells form new capillaries in vivo when there is a need for them, such as during wound repair or when there is a perceived need for them as in tumor formation. The formation of new vessels is termed angiogenesis, and involves molecules (angiogenic factors) which can be mitogenic or chemoattractant for endothelial cells (Klagsburn, supra). During angiogenesis, endothelial cells can migrate out from an existing capillary to begin the formation of a new vessel i.e., the cells of one vessel migrate in a manner which allows for extension of that vessel (Speidel, C. C., *Am J. Anat.* 52: 1–79). In vitro studies have documented both the proliferation and migration of endothelial cells; endothelial cells placed in culture can proliferate and spontaneously develop capillary tubes (Folkman, J., and Haudenschild, C., 1980, *Nature* 288:551–56).

The terms "angiogenic endothelial cells" and "endothelial cells undergoing angiogenesis" and the like are used interchangeably herein to mean endothelial cells (as defined above) undergoing angiogenesis (as defined above). Thus, angiogenic endothelial cells are endothelial cells which are proliferating at a rate far beyond the normal condition of undergoing cell division roughly once a year. The rate of differentiation from normal proliferation of endothelial cells may be 2×, 5×, or 10× or more that of normal proliferation and can vary greatly depending on factors such as the age and condition of the patient, the type of tumor involved, the type of wound, etc. Provided the difference in the degree of proliferation between normal endothelial cells and angiogenic endothelial cells is measurable and considered biologically significant then the two types of cells are differentiable per the present invention, i.e., angiogenic endothelial cells differentiable from corresponding, normal, quiescent endothelial cells in terms of preferential binding of cationic liposomes.

The term "corresponding endothelial cells" "normal or quiescent endothelial cells" and the like are used in order to refer to normal, quiescent endothelial cells contained within the same type of tissue (under normal conditions) when some of the endothelial cells are undergoing angiogenesis and some of the endothelial cells are quiescent. In connection with the present invention, angiogenic endothelial cells are preferentially targeted and are targeted with a preference which is five-fold, preferably ten-fold greater than the targeting of corresponding quiescent endothelial cells.

The term "lipid" is used in its conventional sense as a generic term encompassing fats, lipids, the alcohol-ether-soluble constituents of protoplasm, which are insoluble in water. Lipids compose the fats, fatty oils, essential oils, waxes, steroids, sterols, phospholipids, glycolipids, sulpholipids, aminolipids, chromolipids (lipochromes), and fatty acids. The term encompasses both naturally occurring and synthetically produced lipids. Preferred lipids in connection with the present invention are: phospholipids, including phophatidylcholines and phosphatidylethanolamines, and sphingomyelins. Where there are fatty acids, they could be 12–24 carbons in length, containing up to 6 unsaturations (double bonds), and linked to the backbone by either acyl or ether linkages. Where there is more than one fatty acid linked to the backbone, the fatty acids could be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, or liver, or soybean.

Steroids and sterols, particularly cholesterol, and sterols substituted at the 3b position.

The term "cationic lipid" is used herein to encompass any lipid of the invention (as defined above) which is cationic. The lipid will be determined as being cationic when the lipid has a positive charge (at physiological pH) as measurable by instrumentation utilized at the time of the measurement. Where there are fatty acids present on the cationic lipid, they could be 12–24 carbons in length, containing up to 6 unsaturations (double bonds), and linked to the backbone by either acyl or ether linkages; there could also only be one fatty acid chain linked to the backbone. Where there is more than one fatty acid linked to the backbone, the fatty acids could be different (asymmetric). Mixed formulations are also possible.

The term "liposome" encompasses any compartment enclosed by a lipid bilayer. Liposomes are also referred to as lipid vesicles. In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane. As used in connection with the present invention, the term liposome includes multilamellar liposomes, which generally have a diameter in the range of 1 to 10 micrometers and are comprised of anywhere from two to hundreds of concentric lipid bilayers alternating with layers of an aqueous phase, and also includes unilamellar vesicles which are comprised of a single lipid layer and generally have a diameter of 20 to 100 nanometers which vesicles can be produced by subjecting multilamellar liposomes to ultrasound.

Preferred liposomes would be small unilamellar vesicles (SUVs) which have a single lipid bilayer, and a diameter in the range of 25–200nm.

Preferred polynucleotide (including DNA,RNA and synthetic polynucleotide analogs) liposome complexes would be prepared from the preferred liposomes. Complexes would be prepared such that 1 $\mu$g of polynucleotide is present for every 1–50 nmoles of cationic lipid. When expression from a DNA gene cassette is the desired end product, the optimal ratio of polynucleotide to cationic lipid is determined empirically, by preparing a series of formulations in which a standard amount of DNA is mixed with different amounts of cationic liposome within the range described above. These formulations are then administered in vivo, and the formulation giving the highest expression can be determined.

Cationic liposomes can be functionally defined as having a zeta potential of greater than 0 mV.

The term "cationic liposome" as used herein is intended to encompass any liposome as defined above which is cationic. The liposome is determined as being cationic when present in physiological pH. It should be noted that the liposome itself is the entity which is being determined as cationic meaning that the liposome which has a measurable positive charge within its physiological pH may, within an in vivo environment, become attached to other substances. Those other substances may be negatively charged and thereby result in the formation of a structure which does not have a positive charge. The charge and/or structure of a liposome of the invention present within an in vivo environment has not been precisely determined. However, in accordance with the invention a cationic liposome of the invention will be produced using at least some lipids which are themselves cationic. The liposome need not be comprised completely of cationic lipids but must be comprised of a sufficient amount of cationic lipid such that when the liposome is formed and placed within an in vivo environment at physiological pH the liposome initially has a positive charge.

The term "nucleotide sequence/cationic lipid complex" refers to a combination of a nucleotide sequence which may be an RNA or a DNA sequence which is combined with at least cationic lipids as defined above and may include neutral lipids. When DNA sequences and cationic lipids are combined, they will spontaneously form complexes which are not classical liposomes. The present invention is specifically directed toward the formation of specific nucleotide sequence/cationic lipid complexes wherein the nucleotide sequence is specifically designed to affect angiogenic endothelial cells. For example, the nucleotide sequence may encode a protein which kills angiogenic endothelial cells. The sequence is preferably operatively linked to a promoter which is selectively activated only within the environment of an angiogenic endothelial cell, i.e., not activated within a corresponding, quiescent endothelial cell. Further, the complex may include a sequence which is an antisense sequence which blocks the expression of genetic material within an angiogenic endothelial cell and thereby severely disrupts the operation of and/or kills the angiogenic endothelial cell. The DNA could be plasmid or linear. When a gene product is desired (either a RNA transcript by itself, or translated into a protein), an expression cassette is necessary, which is comprised of a DNA promoter sequence, and a DNA sequence encoding a gene product. Nucleotides with other than phosphodiester bonds are used particularly in antisense uses.

The term "associates with" refers to the action of cationic liposomes of the invention which remain in sufficiently close proximity to angiogenic endothelial cells for sufficiently long periods of time such that the liposome and/or its contents enters the endothelial cell. The liposomes of the invention may associate with angiogenic endothelial cells under a variety of circumstances but, most preferably, associate with the angiogenic endothelial cell when in in vivo conditions. Thus, the liposome may be modified by the attachment, binding or association of other molecules or materials present in the blood stream prior to association with the angiogenic endothelial cell. A variety of forces may be responsible for the association of liposomes with angiogenic endothelial cells such as the non-specific interactions which occur between any two unrelated molecules, i.e., other macromolecules such as human serum albumin and human transferrin. These intermolecular forces may be classified in four general areas which are (1) electrostatic; (2) hydrogen bonding; (3) hydrophobic; and (4) Van der Waals. Electrostatic forces are due to the attraction between oppositely charged ionic groups such as between oppositely charged groups on a cationic liposome and groups present on or in the angiogenic endothelial cell. The force of attraction (F) is inversely proportional to the square of the distance (d) between the charges. Hydrogen bonding forces are provided by the formation of reversible hydrogen bridges between hydrophilic groups. Liposomes of the invention may include hydrophilic groups such as —COOH and similar groups may be present on the surface of endothelial cells as may be the groups —OH, —NH$_2$. These forces are largely dependent on close positioning of two molecules carrying these groups. Hydrophobic forces operate in the same way that oil droplets in water merge to form a single large drop. Accordingly, non-polar hydrophobic groups such as present in the liposomes of the invention tend to associate in an aqueous environment and may tend to associate with hydrophobic groups present on the surface of endothelial cells. Lastly, Van der Waals forces are created between molecules which depend on interactions between the external electron clouds.

The term "selectively associates" and "selectively targets" and the like are used herein to describe a property of cationic liposomes of the invention which causes the cationic liposomes to associate with angiogenic endothelial cells to a higher degree than the cationic liposomes associate with the corresponding normal endothelial cells not involved in angiogenesis. In accordance with the invention selective or preferential association means that the liposome will associate to a five-fold or higher degree with the endothelial cells undergoing angiogenesis as compared with the corresponding normal endothelial cells not undergoing angiogenesis. More preferably, the preferable or selective association indicates a ten-fold or greater selectivity between angiogenic endothelial cells and corresponding normal endothelial cells.

The term "cancer" refers to a disease of inappropriate cell proliferation. This derangement is most evident clinically when tumor tissue bulk compromises the function of vital organs. Concepts describing normal tissue growth are applicable to malignant tissue because normal and malignant tissues can share similar growth characteristics, both at the level of the single cell and at the level of the tissue. Cancer is as much a disease of disordered tissue growth regulation as of disordered cellular growth regulation. Doubling time refers to the time required for a tissue or tumor to double in size or cell number. The doubling time of a clinically apparent tumor is usually considerably longer than the cell cycle time of the cells of which the tumor is composed. However, unlike a tumor, the normal liver, heart, or lungs in an adult do not have a doubling time as the organs are in steady state so that the rates of cell production and cell death are equal (Stockdale, F., 1996, "Cancer growth and chemotherapy," in: *Scientific American Medicine*, vol. 3, Scientific American Press, New York, pp. 12–18). The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al., 1982, "The contribution of blast cell properties to outcome variation in acute myeloblastic leukemia (AML), Blood 59:601–608). For each tumor population, a doubling time exists and a specific growth curve can be established (Stockdale, F., supra). The growth pattern in tumors can be described by a gomperzian curve (Steel, G G, 1977, *Growth kinetics of tumors*, Oxford University Press, Inc., New York, p.40), which indicates that during the development of a tumor the growth rate is initially very rapid and then progressively decreases as size increases.

GENERAL ASPECTS OF THE INVENTION

The attached figures provide a clear visual representation of the highly selective manner in which the cationic liposomes of the invention target angiogenic endothelial cells. A basic embodiment of the invention involves a method of selectively affecting angiogenic endothelial cells by administering (preferably by intravascular injection, more preferably intraarterial injection) a formulation which comprises a pharmaceutically acceptable carrier and cationic liposomes which contain a substance or DNA/cationic complexes. The substance may be a compound which inhibits angiogenesis, a compound which promotes angiogenesis and/or a detectable label. The cationic liposomes within the injected formulation are then allowed to enter angiogenic endothelial cells (by endocytosis) which line the walls of the angiogenic blood vessels. The cationic liposomes associate with the angiogenic endothelial cells for a sufficient period of time and in a manner such that the liposomes themselves and/or the contents of the liposomes enters the angiogenic endothelial cell. Thereafter, the compound which enters the cell can inhibit or promote angiogenesis or merely provide a label allowing the detection of the site of angiogenesis. The selectivity of the targeting of angiogenic endothelial cells can be best understood by referring to the attached figures.

FIG. 1 shows a portion of a mouse ovary having a large round follicle (in yellow) positioned thereon. Because angiogenesis is occurring within a normal mouse ovary, cationic liposomes containing a detectable label associate with angiogenic endothelial cells of the growing blood vessels of the follicle (red-orange). However, within FIG. 1 it is not possible to clearly determine that the label is associated only with angiogenic endothelial cells or whether it is associated with all of the tissue within the ovary and follicle.

Figure 2:
FIG. 2 is a fluorescence micrograph showing the uptake of red fluorescent CM-DiI-labeled DDAB:cholesterol-DNA complexes in angiogenic blood vessels in a section of a pancreatic tumor in a RIP1-Tag5 mouse—vessels stained green with a fluorescent lectin (Scale bar: 40 µm)

FIG. 2 is fluorescence micrograph showing a section of a pancreatic tumor from a mouse which was injected intravenously with cationic liposomes (red-orange) of the invention containing a detectable label. Angiogenesis occurs readily within tumors. Thus, this photo provides some indication that the cationic liposomes (red-orange) of the invention specifically associated with angiogenic endothelial cells (green). However, these results do not dramatically demonstrate the specificity of the invention.

Figure 3:
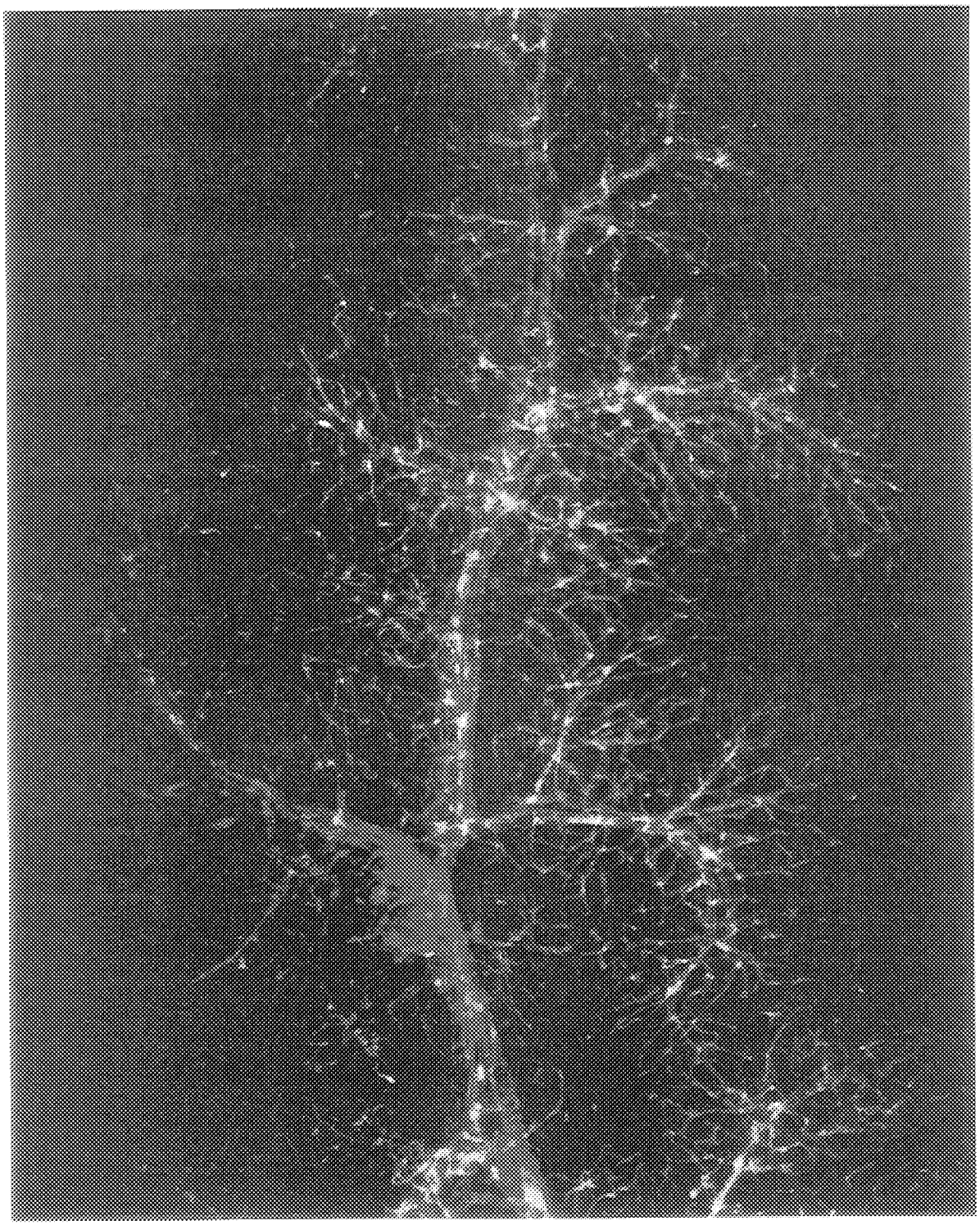
FIG. 3 is a low magnification fluorescence micrograph showing little or no uptake of Texas Red-labeled DOTAP:cholesterol-DNA complexes (yellow-orange) in blood vessels of a normal mouse pancreatic islet (Scale bar: 150 µm )
Figure 4:
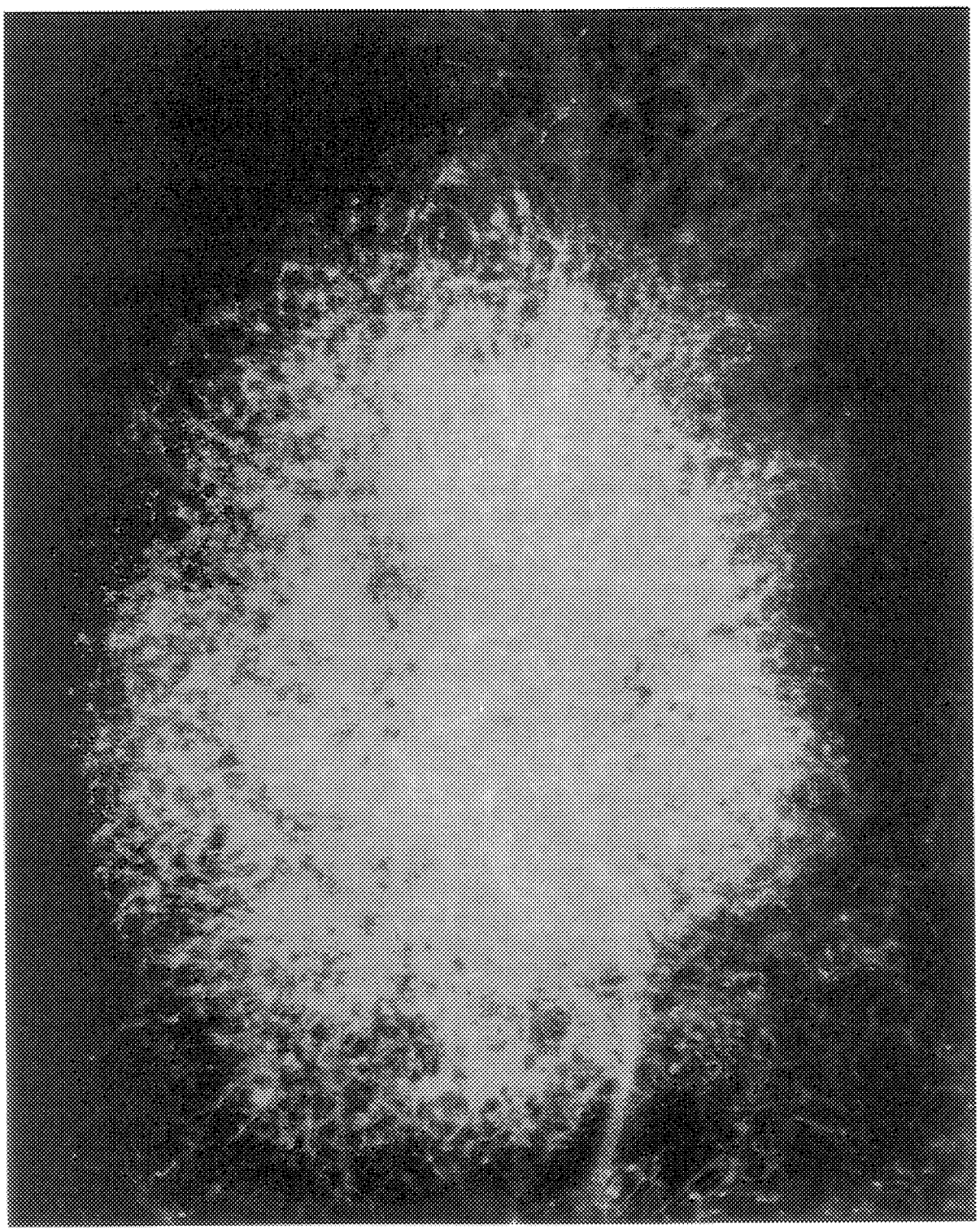
FIG. 4 is a low magnification fluorescence micrograph showing the uptake of Texas Red-labeled DOTAP:cholesterol-DNA complexes (yellow-orange) in blood vessels of a pancreatic tumor in a RIP1-Tag2 mouse (Scale bar: 150 µm)

A comparison of FIGS. 3 and 4 demonstrate the ability of the invention to locate a site of angiogenesis. FIG. 3 is a photo showing blood vessels within normal pancreatic tissue of a mouse. There is much less labeling of the normal endothelial cells than corresponding angiogenic endothelial cells. This is clearly demonstrated by comparing FIG. 3 with FIG. 4 which is a photo of a pancreatic tumor within a mouse. FIG. 4 clearly shows a high degree of accumulation of the label (yellow-orange) contained within the cationic liposomes in the area of a tumor. The dramatic difference between FIGS. 3 and 4 indicate the utility of the present invention to clearly and precisely mark the site of a tumor. However, because so much of the label is associated with the angiogenic blood vessels in FIG. 4, it may not be possible to fully appreciate the specificity of cationic liposomes for preferentially targeting angiogenic endothelial cells.

Figure 5:
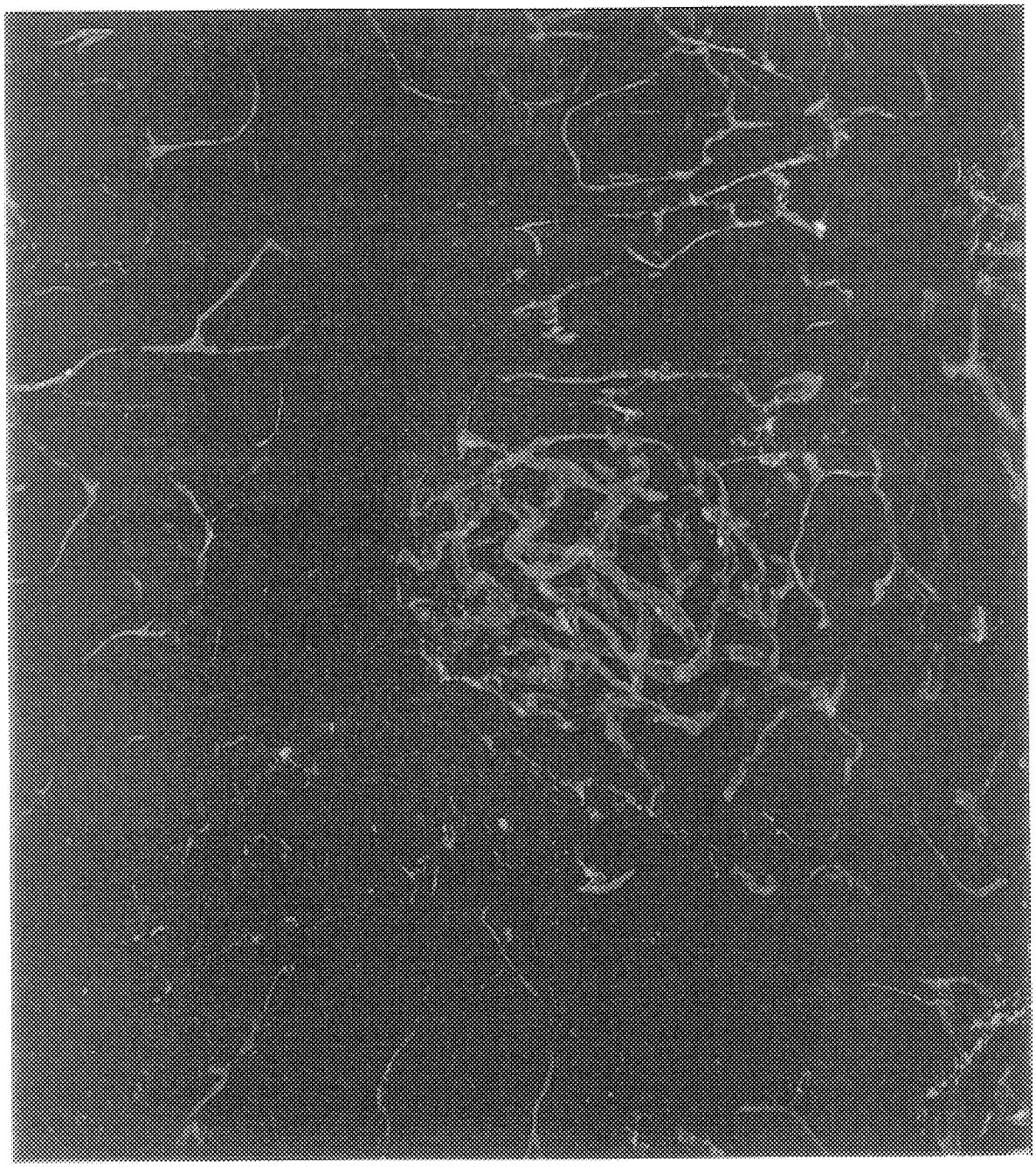
FIG. 5 is a confocal micrograph showing little or no uptake of Texas Red-labeled DOTAP:cholesterol liposomes (red-orange) in a normal pancreatic islet vessels were stained (green) with fluorescent lectin (Scale bar 50 µm)

FIG. 5 is a photo of blood vessels (green) in a normal mouse pancreatic islet. The small amount of red-orange coloring indicates the limited association of cationic liposomes with normal endothelial cells lining the blood vessels of the pancreatic tissue.

Figure 6:
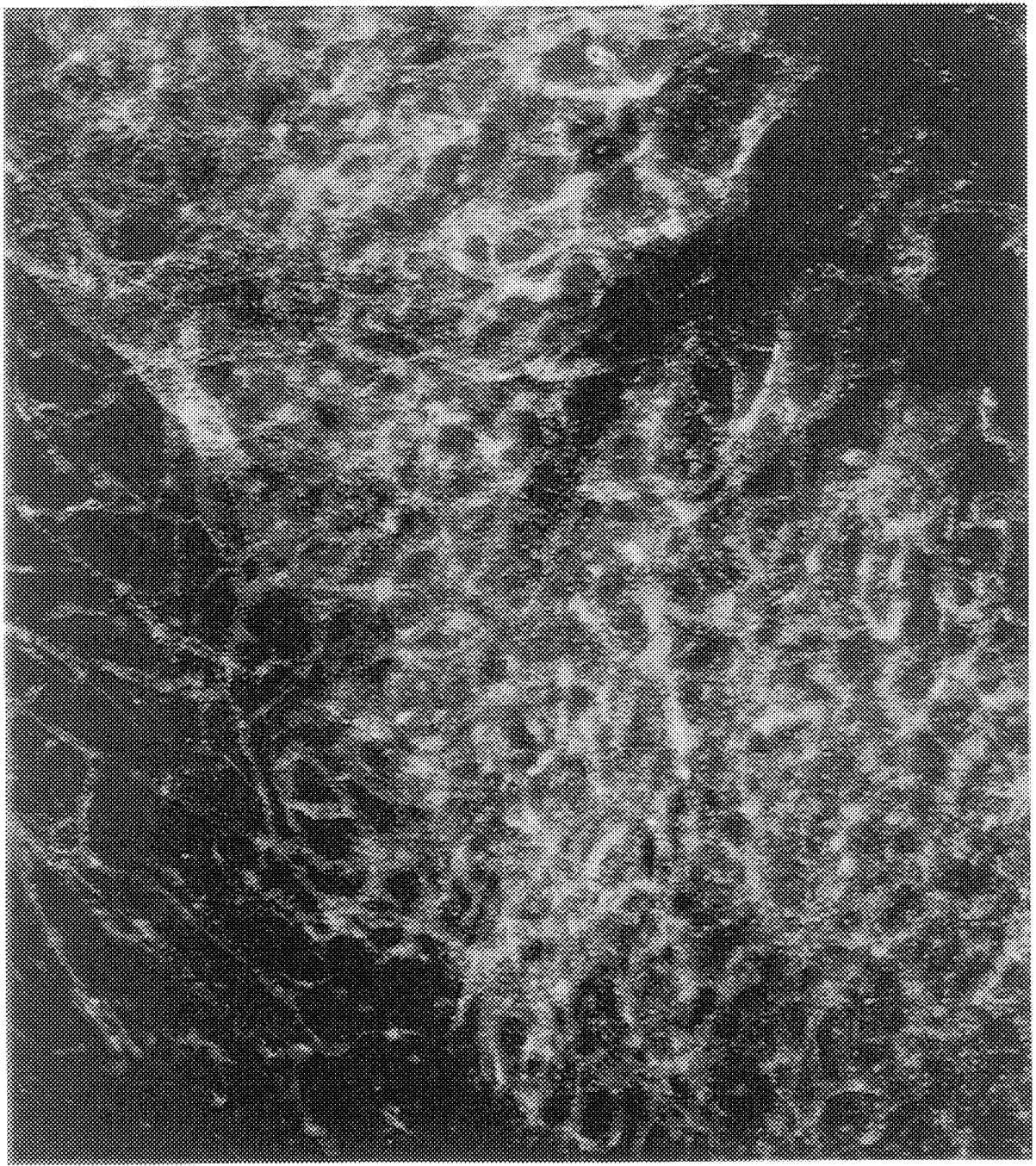
FIG. 6 shows a confocal micrograph of uptake of Texas Red-labeled DOTAP:cholesterol liposomes (red-orange) in a pancreatic tumor in a RIP1-Tag2 mouse. Vessels were stained by perfusion of fluorescent *Lycopersicon esculentum* lectin (green) after liposomes were injected intravenously (Scale bar: 50 µm)

The specificity of the cationic liposomes containing a detectable label is more clearly shown by comparing FIG. 5 with FIG. 6. FIG. 6 clearly shows a much higher degree of accumulation of the label in the endothelial cells of the angiogenic blood vessels of the tumor within the pancreas of a mouse.

Figure 7:
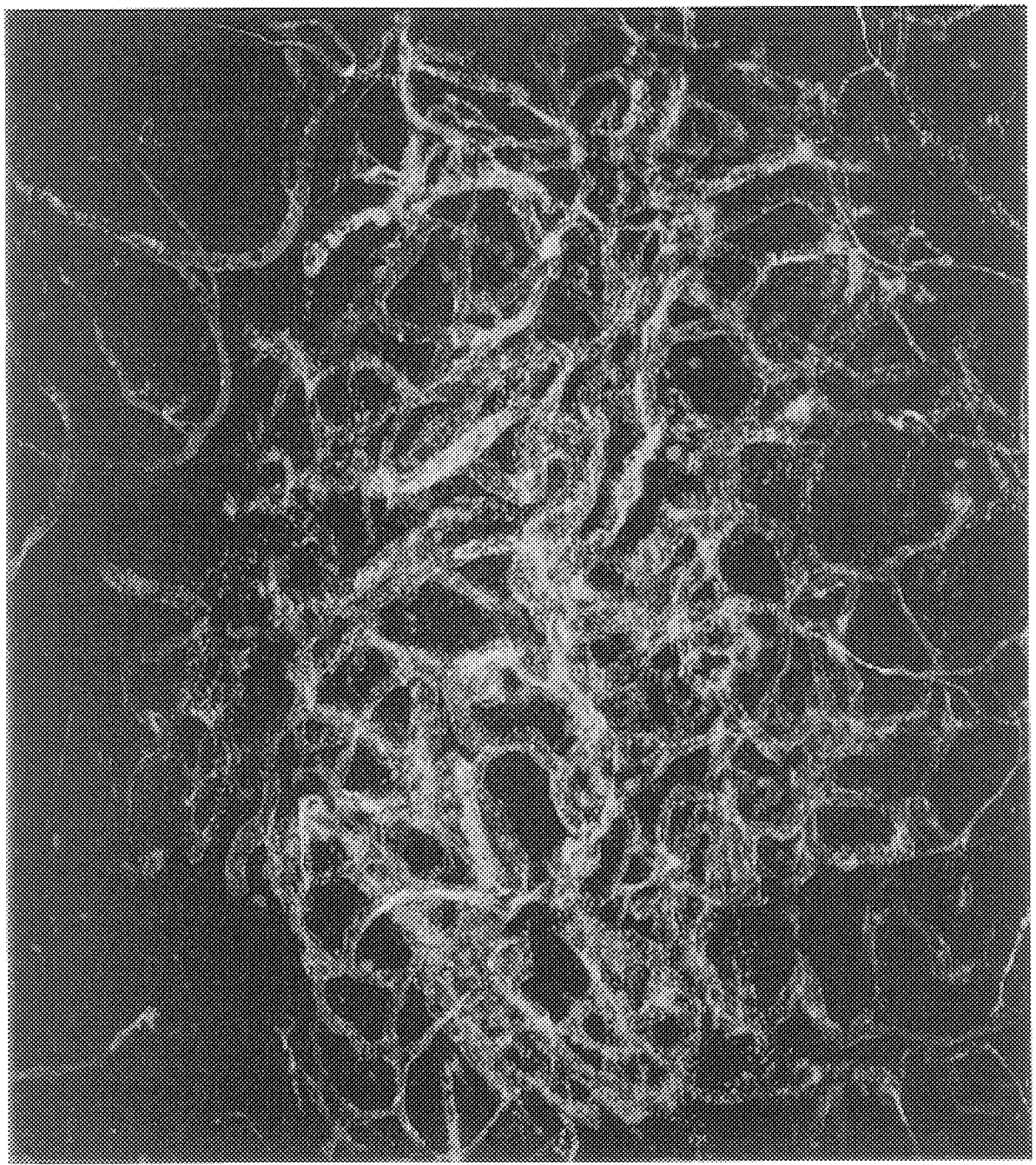
FIG. 7 shows a confocal micrograph of uptake of Texas Red-labeled DOTAP:cholesterol liposomes (red-orange) in a pancreatic tumor in a RIP1-Tag2 mouse. Vessels were stained by perfusion of fluorescent Lycopersicon esculentum lectin (green) after liposomes were injected intravenously (Scale bar: 50 µm)
Figure 8:
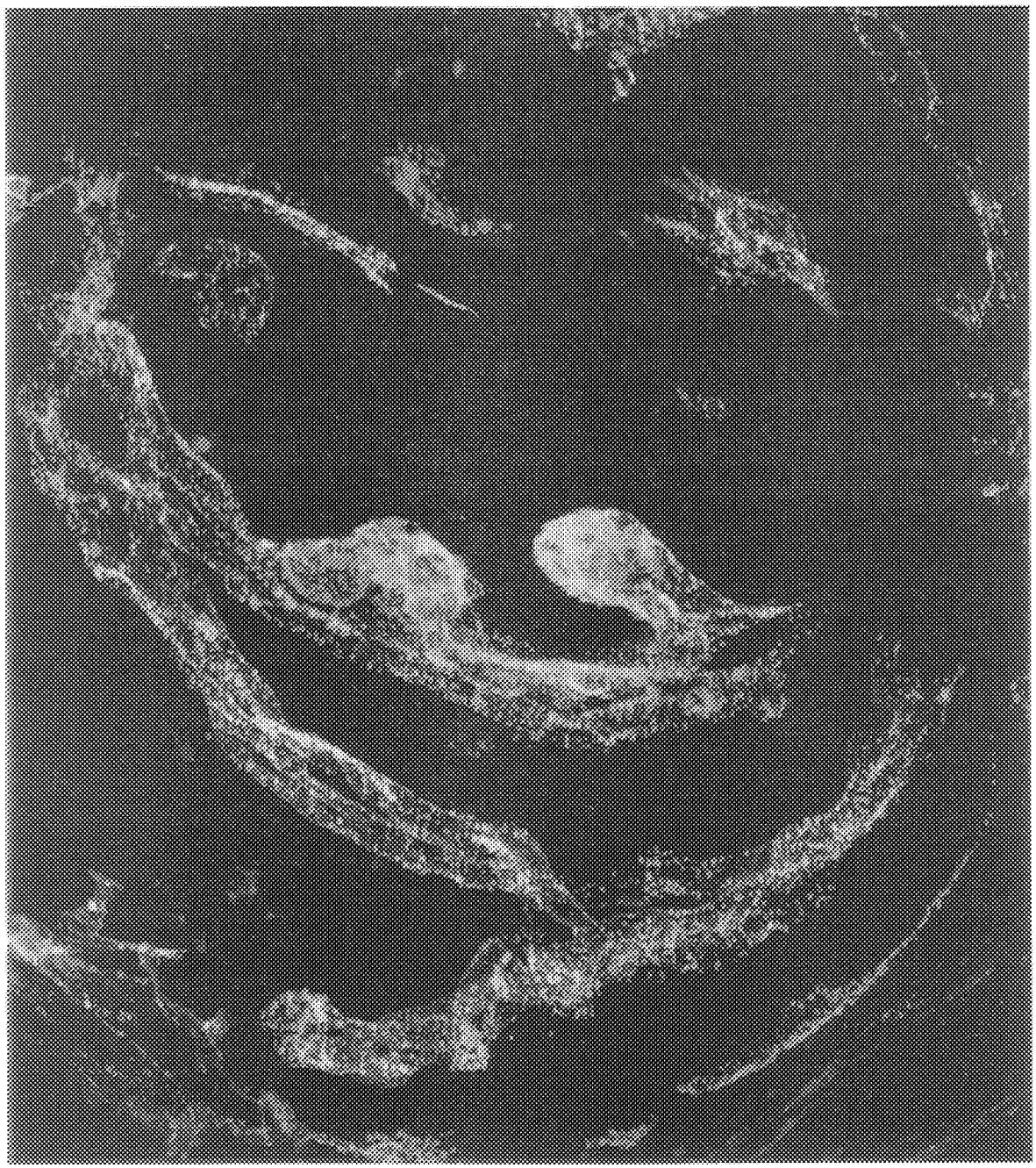
FIG. 8 shows a confocal micrograph of uptake of Texas Red-labeled DOTAP:cholesterol liposomes (red-orange) in a pancreatic tumor in a RIP1-Tag2 mouse. Vessels were stained by perfusion of fluorescent Lycopersicon esculentum lectin (green) after liposomes were injected intravenously. Possible sites of vessel growth have intense uptake (Scale bar: 50 µm)

The precise ability of the cationic liposomes to target angiogenic endothelial cells is dramatically shown within FIGS. 7 and 8. FIG. 7 clearly shows that the fluorescent label is associated only with the blood vessels, i.e., the label is not leaking or migrating into the surrounding tissue. The specificity is most dramatically shown in FIG. 8 which clearly focuses on labelled cationic liposomes detected within angiogenic endothelial cells showing that the label is specific to those cells and not leaking or migrating into the surrounding tissue.

Figure 9:
FIG. 9 is a confocal micrograph showing little uptake of Texas Red-labeled DOTAP:cholesterol liposomes (red-orange) in normal blood vessels in the trachea of a pathogen-free mouse vessels stained green with a fluorescent lectin (Scale bar: 50 µm)
Figure 10:
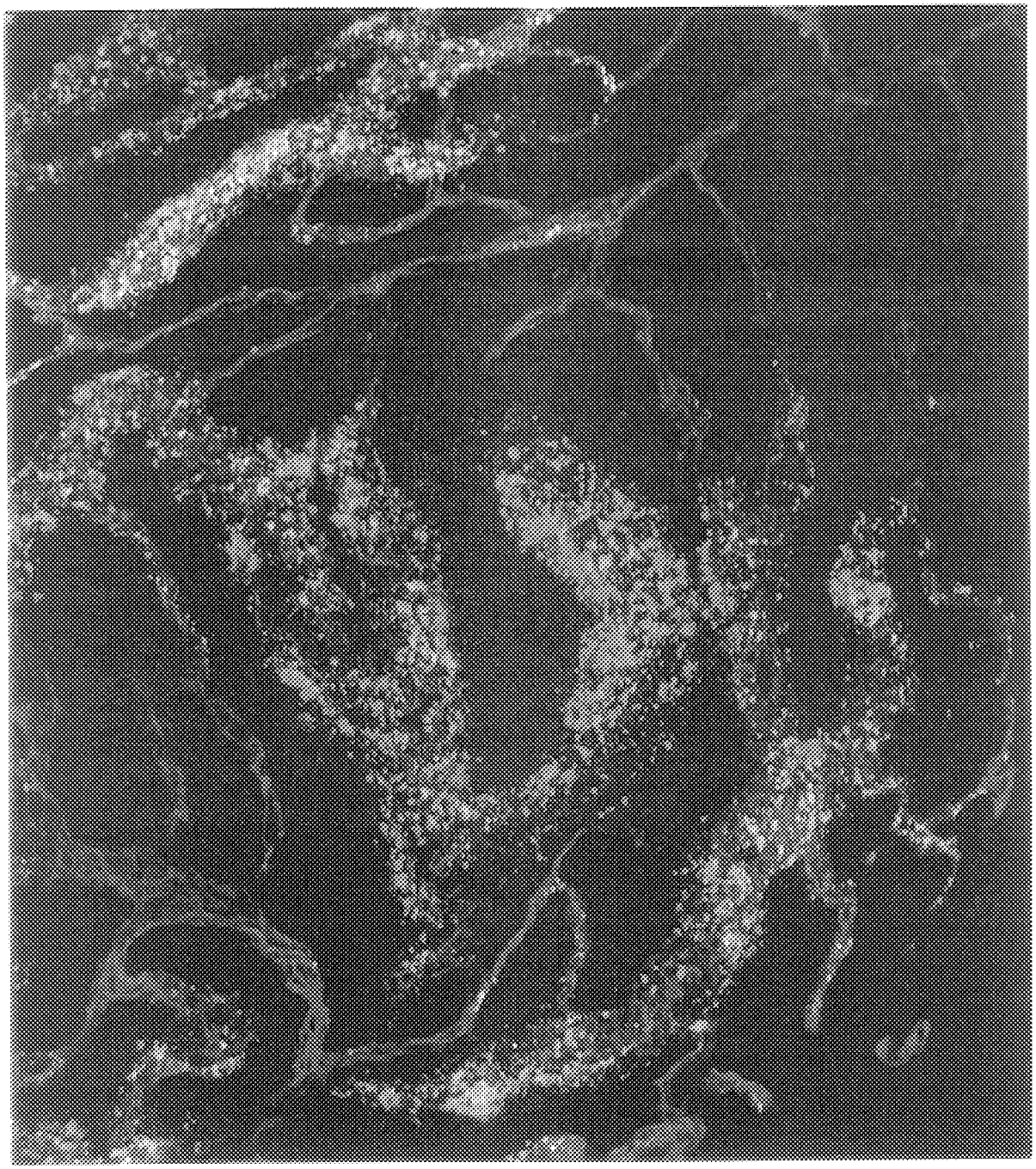
FIG. 10 shows a confocal micrograph of uptake of Texas Red-labeled DOTAP:cholesterol liposomes (red-orange) in angiogenic blood vessels in the trachea of a mouse with *Mycoplasma pulmonis* infection (Scale bar: 50 µm)

FIGS. 9 and 10 demonstrate the same effect described above but with a different model of angiogenesis. FIGS. 1 through 8 were all directed to either normal or cancerous tissue. FIGS. 9 and 10, respectively, show normal and inflamed tissue of the trachea of a mouse. More specifically, FIG. 9 shows the normal blood vessels of a trachea, i.e., a pathogen-free mouse trachea. FIG. 10 shows the blood vessels of a trachea with the occurrence of infection-induced angiogenesis. The higher concentration of the detectable label in FIG. 10 is apparent indicating that the cationic liposomes of the invention selectively associate with angiogenic endothelial cells—specifically associating with endothelial cells of the trachea which have been induced into angiogenesis by an infection.

Figure 11:
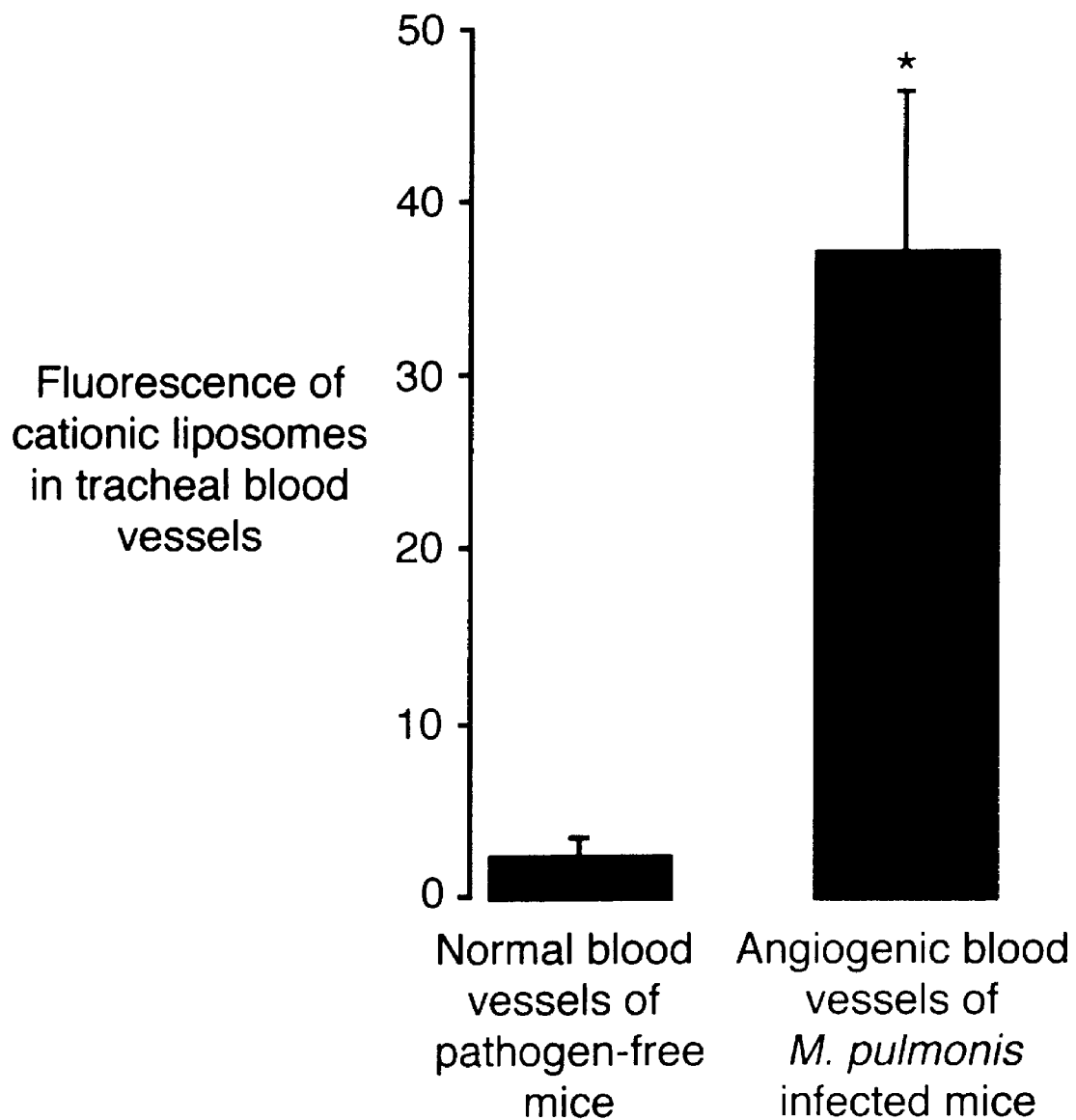
FIG. 11 is a graph showing the amount of uptake of Texas Red-DOTAP:cholesterol liposomes by blood vessels of pathogen-free (normal) and *Mycoplasma pulmonis*-infected mouse tracheas assessed by measuring the intensity of liposome fluorescence 4 hours after intravenous injection. Measurements were made with a Zeiss LSM 410 confocal microscope. Infected mice were inoculated intranasally with *M. pulmonis* organisms and examined 4 weeks later. Asterisk designates statistically significant difference (P<0.05, mean±SE, n=4 mice per group)

FIG. 11 is a graph representing the difference in the specificity of the cationic liposomes between their ability to associate with angiogenic endothelial cells and corresponding normal endothelial cells not undergoing angiogenesis. As shown within FIG. 11, the cationic liposomes of the invention (per this experiment) has shown an approximately 10× greater affinity for angiogenic endothelial cells as compared with corresponding endothelial cells not undergoing angiogenesis.

Figure 12:
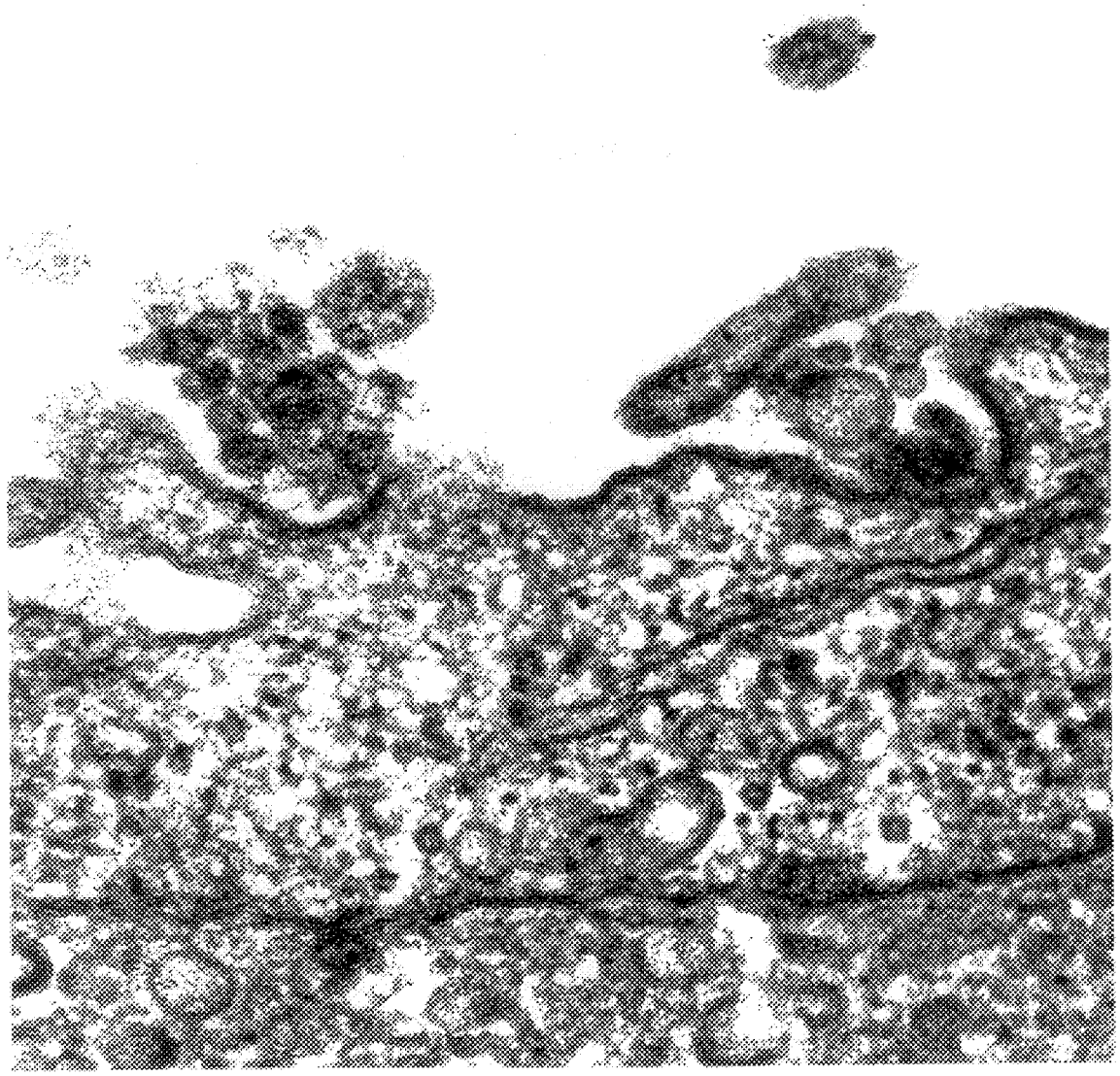
FIG. 12 is a transmission electron micrograph showing DOTAP:cholesterol liposomes associated with an endothelial cell in the trachea of an *M. pulmonis*-infected mouse (Scale bar: 50 µm)
Figure 13:
FIG. 13 is a transmission electron micrograph showing DOTAP:cholesterol liposomes taken up by an endothelial cell in the trachea of an *M. pulmonis*-infected mouse (Scale bar: 80 µm).

Lastly, FIGS. 12 and 13 show how the cationic liposomes of the invention enter the angiogenic endothelial cells. In FIG. 12, cationic liposomes have contacted the surface of the angiogenic endothelial cell. Within FIG. 13, cationic liposomes have entered the angiogenic endothelial cell by endocytosis and are present within the cell.

Having described in words and shown via the figures the specificity of the cationic liposomes of the invention those skilled in the art will be able to produce a variety of different cationic liposomes containing a variety of different substances in order to make use of the invention. However, for completeness the following is a description of cationic liposomes and their methods of manufacture followed by a description of substances which either inhibit or promote angiogenesis.

LIPOSOMES

Liposomes can be readily formed by placing lipids (as defined above) which will include cationic lipids (as defined above) in an aqueous solution and agitating the solution for a period of time of several seconds to hours. The simple procedure spontaneously yields large, multilamellar liposomes or vesicles with diameters in the range of about 1 to 10 micrometers. These liposomes are comprised of two to several hundred concentric lipid bilayers which may alternate with layers of the aqueous phase which the lipids were present within. A substance such as a compound which inhibits angiogenesis, promotes angiogenesis or provides for a detectable label can be included within the aqueous phase. The substance is preferably water soluble or can, at least, be readily dispersed in water.

The thickness of the aqueous layer and thus the total amount of aqueous phase trapped within the liposome, depends on the balance of electrostatic repulsion forces between charged lipids and Van der Waals attractive forces between bilayers as a whole. Thus, the aqueous spacing (and hence the volume of aqueous material trapped) increases with increasing proportion of charged lipids in the membrane and with decreasing concentrations of electrolytes (charged ions) in the aqueous phase. The small liposomes or vesicles formed are unilamellar and have a size in the range of about 20 to 100 nanometers and can be produced by subjecting multi-lamellar vesicles to ultrasound. Larger unilamellar liposomes having a size in the range of about 0.1 to 1 $\mu$m in diameter can be obtained when the lipid is solubilized in an organic solvent or a detergent and the solubilized agent is removed by evaporation or dialysis, respectively. The fusion of smaller unilamellar liposomes by methods requiring particular lipids or stringent dehydration-hydration conditions can yield unilamellar vessels as large or larger than cells.

In order to form cationic liposomes of the invention it is necessary that the liposomes be produced using at least some cationic lipid. However, the cationic liposomes of the invention do not need be comprised entirely of cationic lipids. For example, using neutral lipids in an amount of about 45% and cationic lipids in an amount of about 55% will yield cationic lipids which are useful in connection with the invention and preferentially target angiogenic endothelial cells.

The compounding of cationic liposomes with a substance which affects angiogenesis and/or a label includes the liposome preparation wherein liposomes are prepared according to standard technology whereby, for example, solutions of 1-{2-(9(Z)-octadecenoyloxy)ethyl}-2-(8(Z)-heptadecenyl) 3-(2-hydroxyethyl) imidazolinium chloride 9DOTAP), cholesterol, and Texas Red DHPE are mixed, evaporated to dryness and the lipid film is subsequently rehydrated in 5% dextrose to yield multi lamellar vesicles. These vesicles are extruded through polycarbonate membrane filters to yield unilamellar vesicles. Liposomes and the substance to be compounded, for example plasmid DNA, are mixed together in specific ratios in a 5% dextrose solution or other physiologically acceptable excipient. Useful cationic lipids include: DDAB, dimethyldioctadecyl ammonium bromide [available from Avanti Polar Lipids and Sigma Chemical Company] 1,2-diacyl-3-trimethylammonium-propanes, (including but not limited to, dioleoyl (DOTAP), dimyristoyl, dipalmitoyl, disearoyl) [these are all available from Avanti Polar Lipids]; 1,2-diacyl-3-dimethylammonium-propanes, (including but not limited to, dioleoyl, dimyristoyl, dipalmitoyl, disearoyl) [these are all available from Avanti Polar Lipids] DOTMA, N-[1-[2,3-bis (oleoyloxy)]propyl]-N,N,N-trimethylammonium chloride, DOGS, dioctadecylamidoglycylspermine [available from Promega Corporation] DC-cholesterol, 3b- [N-(N',N'-dimethylaminoethane)carbamoyl]cholesterol DOSPA, 2,3-dioleoyloxy-N-(2(sperminecarboxamido)ethyl)-N,N-dimethyl-1-propanaminium trifluoroacetate, 1,2-diacyl-sn-glycero-3-ethylphosphocholines (including but not limited to dioleoyl (DOEPC), dilauroyl, dimyristoyl, dipalmitoyl, distearoyl, palmitoyl-oleoyl) [these are all available from Avanti Polar Lipids]; b-alanyl cholesterol, CTAB, cetyl trimethyl ammonium bromide diC14-amidine, N-t-butyl-N'-tetradecyl-3-tetradecylaminopropionamidine, 14Dea2, O,O'-ditetradecanolyl-N-(trimethylammonioacetyl) diethanolamine chloride, (N,N,N',N'-tetramethyl-N,N'-bis(2-hydroxylethyl)-2,3-diol eoyloxy-1,4-butanediammonium iodide [available from Promega Corporation] 1-[2-acyloxy)ethyl]2-alkyl (alkenyl)-3-(2-hydroxyethyl)imidazolinium chloride derivatives such as 1-[2-(9(Z)-octadecenoyloxy) ethyl]-2-(8(Z)-heptadecenyl-3-(2-hydroxyethyl) imidazolinium chloride (DOTIM), 1-[2-(hexadecanoyloxy) ethyl]-2-pentadecyl-3-(2-hydroxyeth yl)imidazolinium chloride (DPTIM); 1-[2-tetradecanoyloxy)ethyl]-2-tridecyl-3-(2-hydroxyethyl)imidazolium chloride (DMTIM)—these 3 lipids are described in Solodin et al, Biochem 43, 135737-13544, 1995. This is from Tim Heath's lab in Wisconsin; Megabios have acquired the patents for some of his lipid inventions.

2,3-dialkyloxypropyl quaternary ammonium compound derivates, containing a hydroxyalkyl moiety on the quaternary amine, such as 1,2-dioleoyl-3-dimethylhydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP); 1,2-dioleyloxypropyl-3-dimethyl-hydroxybutyl ammonium bromide (DORIE-HB); 1,2-dioleyloxypropyl-3-dimethylhydroxypentyl ammonium bromide (DORIE-HPe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DSRIE)—these lipids were developed by Vical, Felgner et al., J. Biol. Chem. 269, 2550–2561, 1994.

Cationic liposomes are prepared from the cationic lipids themselves, or in admixture with other lipids, particularly neutral lipids such as:
CHOLESTEROL
1,2-diacyl-sn-glycero-3-phosphoethanolamines, (including but not limited to dioleoyl (DOPE); a large family of derivatives is available from Avanti Polar Lipids);
1,2-diacyl-sn-glycero-3-phosphocholines (a large family of derivatives is available from Avanti Polar Lipids);
N.B. One could include asymmetric fatty acids, both synthetic and natural, and mixed formulations, for the above diacyl derivatives.

Liposomes of the type described above and of other types which occur to those skilled in the art can be used in the present invention with the liposomes containing a substance which either promotes or inhibits angiogenesis and/or includes a detectable label. One example of liposomes of the invention are cationic liposomes containing a lipid soluble or water soluble substance which inhibits angiogenesis. However, lipid soluble compounds may be in the lipid bilayer. The following provides a description of angiogenesis inhibitors. However, it should be noted that others will occur to those skilled in the art and/or will be developed after the present invention and that such inhibitors of angiogenesis could be readily used in connection with the present invention.

ANGIOGENESIS INHIBITING AGENTS

Heparin is a potentiator of angiogenesis, and heparin antagonists can block the angiogenic response. Protamine, a heparin binding protein, displays antiangiogenic properties (Taylor, S. and Folkman, J., 1982, "Protamine is an inhibitor of angiogenesis," Nature, 297, 307), but is not clinically useful because it is known to cause anaphylactic reactions upon exposure in humans. Another anti-angiogenic agent is the heparin binding protein, Major Basic Protein, which is also highly toxic and thus not practical for human use. However, because of the high degree of targeting selectivity obtained with the present invention these and other compounds which inhibit angiogenesis but are thought to be too toxic for therapeutic use on humans may well be useful because they can be used in very small amounts.

Platelet factor 4 (PF4) displays both heparin-binding activity and anti-angiogenic properties, and since it is not as toxic as the other heparin antagonists may be clinically useful. Chemical modifications of PF4, as disclosed in U.S. Pat. No. 5,112,946, enhance PF4's anti-angiogenic properties. These modifications include the production of PF4 analogs modified through their free amino groups with fluorescein-isothiocyanate, PF4 mutants with specifically altered structural composition of the protein, and the production of PF4 fragments that retain the anti-angiogenic properties. In particular, a synthetic peptide of 13 amino acids corresponding to the carboxy terminus of PF4 has displayed potent angiostatic activity.

A variety of steroids have been shown to inhibit angiogenesis. This anti-angiogenic activity is potentiated by the addition of heparin or related molecules (Folkman, J., Weisz, P. B., et al., 1989, "Control of angiogenesis with synthetic heparin substitutes," Science 243, 1490–3). The so-called "angiostatic steroids," such as tetrahydrocortisone, have the ability to block angiogenesis in vivo. Specifically, 6α-fluoro-17,21-dihydroxy-16β-methylpregna-4,9-(11)-diene-3,20-dione has been used as a potent angiostatic steroid.

Drugs that modulate collagen metabolism have been found to inhibit angiogenesis. Analogs of the amino acid proline specifically inhibit collagen synthesis and inhibit angiogenesis in vivo. Specifically, L-azetidine-2-carboxylic acid (LACA), cis-hydroxyproline (CHP), D,L-3,4-dehydroproline (DHP), and thioproline (TP) each display anti-angiogenic activity in order of descending activity (Ingber, D., and Folkman, J., 1988, "Inhibition of angiogenesis through modulation of collagen metabolism," 1988, Lab. Invest. 59, 44–51). Each of these analogs also potentiates the anti-angiogenic effects of angiostatic steroids and heparin.

Human thrombospondin, a glycoprotein found in the alpha granules of platelets, inhibits angiogenesis in trimer or monomer or fragment form, as disclosed in U.S. Pat. No. 5,192,744. Each work in the glycosylated form, and are predicted to work in the unglycosylated form. The angiogenesis-inhibiting properties are present following deletion of the heparin binding domain associated with the amino end and the platelet binding domain found at the carboxyl end of the monomeric protein.

Peptides displaying laminin activity block angiogenesis and prevent the formation of excess blood vessels in tissues. Specific peptides with such activity are: 1) tyrosine-isoleucine-glycine-serine-arginine; 2) proline-aspartine-serine-glycine-arginine; and 3) cysteine-aspartate-proline-glycine-tyrosine-isoleucine-glycine-serine-arginine. These peptides are predicted to maintain their anti-angiogenic activity in a cyclic form.

Other examples of angiogenesis-inhibiting substances include extracts from cartilage tissue showing collagenase activity, protein derived from retinal pigment endothelial cells (Arch. Ophthamol., 103, 1870 (1985), anti-cancer factor induced from cultured cartilage cells (Takigawa, M. and Suzuki, F., 1988, "Establishment of clonal cell lines producing cartilage-derived anti-tumor factor (CATF), *Protein, Nucleic Acid and Enzyme,* 33, 1803–7), anti-inflammatory drugs such as indomethacin (Peterson, H. I., 1986, "Tumor angiogenesis inhibition by prostaglandin sythease inhibitors," *Anticancer Res.,* 6, 251–3), ribonuclease inhibitors (Shapiro, R., and Vallee, B. L., 1987, "Human placental ribonuclease inhibitor abolishes both angiogenic and ribonucleolytic activities of angiogenin," *PNAS* 84, 2238–41), complexes of sulfuric polysaccharide and peptide gaycan (e.g. JPA-S63(1988)-119500), gold preparations for arthritis, herbimycin A (JPA-S63(1988) 295509) and fumagillin or fumagillol derivatives. A number of fumagillol derivative have angiogenesis-inhibiting properties, as disclosed in U.S. Pat. No. 5,202,352. The above references are incorporated by reference to describe and disclose inhibitors of angiogenesis.

ANGIOGENIC FACTORS

A number of biological compounds stimulate angiogenesis. Angiogenin has been shown to be a potent angiogenic factor in the chick CAM or rabbit cornea. Angiotrophin, a factor isolated in peripheral blood monocytes, is another angiogenic compound that has been proposed to play a role in normal wound healing (Biochemistry 27, 6282 (1988)). Other factors involved in wound healing, such as fibrin, also induce ascularization.

Another class of mediators of angiogenesis are olypeptide angiogenic factors such as growth factors, which includes acidic and basic fibroblast growth factors (FGFs), transforming growth factor alpha (TGF-$\alpha$) and platelet-derived growth factor (PDGF). Each of these molecules has been shown to induce angiogenesis in vivo. Other similar molecules that display angiogenic activity are vascular endothelial growth factor (VEGF), tumor necrosis factor alpha (TNF-$\alpha$), transforming growth factor beta (TGF-$\beta$), and the heparin binding growth factors (HBGFs).

Other angiogenic factors have been described in addition to polypeptide angiogenic factors. Prostaglandins $E_1$ and $E_2$, which are lipid-derived angiogenic factors, are well known inflammatory cell attractants with angiogenic properties (*J. Natl. Cancer Inst.* 69, 475–482 (1982)). Nicotinamide causes an angiogenic response when tested in chick cornea or in a chick CAM assay (*Science* 236, 843–845 (1987)).

DETECTABLE LABELS

The cationic liposomes of the invention can be used to deliver detectable labels of any sort. The labels are either soluble in the lipid used to make the liposomes, or they are soluble or, at least, dispersable within water or an aqueous solution such as an aqueous saline or aqueous dextrose solution. The label may be a radioactive label, fluorescent label, histochemically or immunohistochemically detectable substance, or detectable dye. The label may be present in any appropriate amount and may be included in or complexed with, the liposome by itself or along with a substance which inhibits or promotes angiogenesis.

DOSING

The amount of angiogenic inhibitor or promoter administered to a patient (which may be any animal with a circulatory system with endothelial cells which undergo angiogenesis) will vary depending on a wide range of factors. For example, it would be necessary to provide substantially larger doses to humans than to smaller animals. The amount of angiogenic inhibitor or promoter will depend upon the size, age, sex, weight, and condition of the patient as well as the potency of the substance being administered. Having indicated that there is considerable variability in terms of dosing, it is believed that those skilled in the art can, using the present disclosure, readily determine appropriate dosing by first administering extremely small amounts and incrementally increasing the dose until the desired results are obtained. Although the amount of the dose will vary greatly based on factors as described above, in general, the present invention makes it possible to administer substantially smaller amounts of any substance as compared with delivery systems which target the surrounding tissue e.g., target the tumor cells themselves.

NUCLEOTIDE SEQUENCE/CATIONIC LIPID COMPLEXES

When nucleotide sequences including DNA and RNA sequences are combined with lipids, the two form complexes. By choosing the particular amounts of nucleotide sequences and lipids and choosing particular lipids, it is possible to form complexes which do not aggregate together in vitro. General information relating to the formation of such complexes are described within PCT publication WO 93/12240, published Jun. 24, 1993, which is incorporated herein by reference, to specifically disclose and describe the formation of nucleotide sequence/lipid complexes. In connection with the present invention, the nucleotide sequences are designed specifically to affect angiogenic endothelial cells and not to affect other cells and specifically not to affect other corresponding endothelial cells, i.e., quiescent endothelial cells. The DNA sequences used in connection with the present invention are operably linked to promoters and those promoters are specifically designed so that the expression of the nucleotide sequence is obtained only within the environment of an angiogenic endothelial cell. Firstly, the promoter can be an activatable promoter which can be activated after the sequence has been delivered to an angiogenic endothelial cell. More preferably, the promoter is designed such that it is activated within the specific environment of an angiogenic endothelial cell. There are a number of naturally occurring phenomena within the environment of an angiogenic endothelial cell which are not occurring within the environment of a quiescent endothelial cell. By taking advantage of the differences between the two types of cells, the promoter is specifically designed so that it is activated only in the presence of an angiogenic endothelial cell.

Transcription from DNA cassettes could be restricted to a single or narrow range of cell types using a specific gene promoter. Endothelial cells selectively express several proteins for which genes and their promoters have been elucidated. The vascular endothelial growth factor (VEGF) receptors flt-1 and flk-1 gene promoters, the von Willibrand factor (VWF) gene promoter, and the tie family gene promoters have shown to direct selective expression in endothelial cells when linked to reporter gene constructs. The following publications are cited to disclose and describe promoters which are activated in angiogenic endothelial cells.

Hatva, E., et al, 1996, "Vascular growth factors and receptors in capillary hemangioblastomas and hemangiopericytomas," Am. J. Path. 148: 763–75;

Strawn, L. M., et al., 1996, "Flk-1 as a target for tumor growth inhibition," Cancer Res. 56: 3540–5;

Millauer, B., et al., 1996, "Dominant-negative inhibition of Flk-1 suppresses the growth of many tumor types in vivo," Cancer Res. 56: 1615–20;

Sato, T. N., et al., 1996, "Distinct roles of the receptor tyrosine kinases Tie-1 and Tie-2 in blood vessel formation," Nature 376: 70–4;

Ozaki, K., et al., 1996, "Use of von Willebrand factor promoter to transduce suicidal gene to human endothelial cells, HUVEC," Human Gene Therapy: 13 1483–90;

Ronicke, V., et al., 1996, "Characterization of the endothelium-specific murine vascular endothelial growth factor receptor-2 (Flk-1) promoter," Circulation Res. 79: 277–85;

Shima, D. T., et al., 1996, "The mouse gene for vascular endothelial growth factor. Genomic structure, definition of the transcriptional unit, and characterization of transcriptional and post-transcriptional regulatory sequences," J. Biol. Chem. 271: 3877–8;

Morishita, K., et al, 1995, "A novel promoter for vascular endothelial growth factor receptor (flt-1) that confers endothelial-specific gene expression," J. Biol. Chem. 270: 27948–53;

Patterson, C., et al., 1995, "Cloning and functional analysis of the promoter for KDR/flk-1, a receptor for vascular endothelial growth factor," J. Biol. Chem. 270: 23111–8;

Korhonen, J., et al., 1995, "Endothelial-specific gene expression directed by the tie gene promoter in vivo," Blood 86: 1828–35.

N.B. The Ozaki reference describes another useful approach-that of expressing herpes simplex virus thymidine kinase (TK) in endothelial cells, and subsequent treatment with the prodrug ganciclovir.

Alternatively, the nucleotide sequence can be an antisense sequence which will bind to sequences which must be expressed within an angiogenic endothelial cell thereby blocking the expression of naturally occurring sequences of an angiogenic endothelial cell which are necessary for the survival of that cell.

CLOT FORMATION

Another aspect of the invention which may be carried out using liposomes or nucleotide sequence/lipid complexes involves the formation of blood clots. Specifically, the liposome or complex of the invention is designed so that it has an effect on angiogenic endothelial cells resulting in the formation of blood clots in the angiogenic blood vessels. The blood clots prevent the flow of nutrients and oxygen to the remainder of the vessel, resulting in the death of the vessel and the surrounding tissue.

The basic concept of forming clots within tumor vasculature in order to eliminate an undesired tumor has been carried out using antibodies to target the tumor vascular. The present invention could achieve improved results using cationic lipids which lipids contain an agent which promotes the thrombogenic cascades. For example cationic liposomes of the invention could be constructed to encompass human tissue factor (TF) which is the major initiating receptor of the thrombotic (blood coagulation cascades).

Tumor cells are dependent on blood supply. The local interruption of the tumor vasculature will produce an avalanche of tumor cell death. The tumor vascular endothelium is in direct contact with the blood. However, tumor cells themselves are outside the blood stream and for the most part, poorly accessible to many materials injected into the circulatory system. This aspect as well as other aspects of the invention work particularly well in that the cells being targeted are the angiogenic endothelial cells which are themselves not transformed i.e., are cells which are unlikely to acquire mutations which render them resistant to therapy. The tumor cells undergo considerable mutations and such mutations often render the cells resistant to therapy. Results with respect to decreasing the size of tumors using antibody-directed targeting have been taught by others as follows: Burrows, F. J., and P. E. Thorpe. Eradication of large tumors in mice with an immunotoxin directed against tumor vasculature, *Proc Natl Acad Sci U.S.A.* 90:8996–9000, 1993. Huang, X., G. Molema, S. King, L. Watkins, T. S. Edgington, and P. E. Thorpe, Tumor infarction in mice by antibody-directed targeting of tissue factor to tumor vasculature, *Science* 275:547–550, 1997.

In order to carry out clot formation in connection with the present invention it is preferable to form a DNA/cationic lipid complex. The complex will include DNA which encodes a protein such as human tissue factor which protein is a major initiating receptor for the thrombotic (blood coagulation) cascades. The gene encoding TF is preferably operatively linked to a promoter which promoter is activated in the environment of an angiogenic endothelial cell and not activated within the environment of a quiescent endothelial cell. Thus, the cationic lipids of the complex will cause the complex to associate with angiogenic endothelial cells. Thereafter, the complex will be brought within the angiogenic endothelial cell and the DNA of the complex will be expressed. The expressed protein will initiate the blood coagulation cascade. When blood clots are formed within the vessel further oxygen and nutrient supply to the surrounding tumor cells will be cut off. Thereafter, the tumor cells will die. Variations on human tissue factor such as truncated human tissue factor (tTF) can also be used to initiate clotting. Genetic material encoding tTF and other factors is known (see the above cited Huang, et al reference and the publication cited therein).

EXPERIMENTAL MODELS OF ANGIOGENESIS

The present invention was facilitated by use of rodent models for angiogenesis. Chronic inflammatory diseases such as asthma and bronchitis induce tissue and vascular remodeling in the airway mucosa. To learn about the pathogenesis of chronic airway inflammation, a model was used wherein chronic inflammation and tissue remodeling occurs in tracheas of rats and mice. Angiogenesis develops in the airway mucosa as the result of *Mycoplasma pulmonis* infection. In this model, *Mycoplasma pulmonis* organisms cause a persistent infection in the tracheal and bronchial epithelium. The airway mucosa of rats infected with *M. pulmonis* has several distinct abnormalities: 1) thickening of the epithelium and lamina propria; 2) changes in the cellular composition of the epithelium 3) angiogenesis; 4) increased sensitivity of the angiogenic vessels to the inflammatory mediator substance P in terms of plasma leakage; 5) substance P-induced leakage from capillaries as well as venules; and 6) increased number of receptors for substance P (NK1 receptors) on capillary endothelial cells. In this model, angiogenesis is driven by chronic inflammation, and the blood vessels are more susceptible to inflammatory mediators.

Studies using perfusion of lectins to stain the luminal endothelial cell surface revealed the extent of angiogenesis in rats after *M. pulmonis* infection. Numerous capillary-like vessels are present in the tracheal mucosa of infected rats, and these vessels leak following intravenous injection of the inflammatory mediator substance P.

In mice, *M. pulmonis* causes an acute pulmonary inflammation that peaks 6–9 days after inoculation followed by persistent infection of the airways. The response of mice to infection by *M. pulmonis* is very dependent upon strain: for example, C3H strains show higher mortality and greater reduction of the cytokine tumor necrosis factor-α than C57 BL strains. Some aspects of mucosal remodeling, such as epithelial hyperplasia, have been described in the airways of mice infected by *M. pulmonis*. In C57BL/6 mice infected with nasal inoculation of *M. pulmonis*, the number of tracheal vessels increases dramatically, apparently via growth of new capillaries. In this strain, the tracheal mucosal vasculature is no longer planar, and small vessels grow perpendicular to the plane of the mucosa. Numerous apparent vascular sprouts are found in regions of increased vascularity. Thus, infection of C57BL/6 mice by *M. pulmonis* produces chronic airway inflammation with endothelial proliferation, vascular remodeling, and angiogenesis. In contract, in C3H/HeNCr mice infected by nasal inoculation of *M. pulmonis*, the number of vascular endothelial cells in the tracheal mucosa increases but the number of vessels does not. The increased vascularity is not due to an increase in length or number of vessels but to an increase in vessel diameter, and this increase in vessel size is due to a doubling of the number of endothelial cells. The size of individual endothelial cells in infected tracheas does not increase significantly. The levels of circulating antibodies to *M. pulmonis* are similar in the two strains of mice. Thus, infection of C3H/HeNCr mice by *M. pulmonis* produces chronic airway infection with vascular remodeling and endothelial proliferation but not a significant increase in the number of vessels, while that in C57BL/6 mice produces endothelial proliferation and new vessels.

In a second model, angiogenesis occurs in tumors that result from transgenic expression of the SV40 viral oncogene. The "RIP-Tag" transgenic mouse model provides the opportunity to study the phenotypic changes in angiogenic endothelial cells in a well characterized progression from normal tissue to tumors. In the "RIP-Tag" transgenic mouse model, the oncogene from the SV-40 virus, large T antigen (Tag), is driven by a region of the rat insulin promoter (RIP). When inserted into the murine genome, this construct induces Tag expression specifically in pancreatic islet β-cells, which are localized in approximately 400 islets scattered throughout the pancreas. All of the islets of the pancreas in these mice express Tag, however the islets develop normally until approximately age 6 weeks. After this point, approximately 50% of the islets become hyperplastic. However, of these hyperplastic islets, a small fraction (<5%) develop into tumors by approximately weeks. This bottleneck in tumorigenesis appears to be overcome when an islet acquires the ability to induce angiogenesis: hence this phase of tumorigenesis has been termed the "angiogenic switch." A similar angiogenic switch also appears to exist in other models of murine tumorigenesis as well as in several human tumors. Thus, the RIP-Tag model provides a well characterized framework for examining the progression of angiogenesis in tumors.

EXAMPLES

The following examples are put forth so as to provide those of ordinary skill in the art with a complete disclosure and description of how to make cationic liposomes and carry out the methodology for using such liposomes, and are not intended to limit the scope of what is regarded as the invention. Efforts have been made to insure accuracy with respect to numbers used (e.g., amounts, temperature, etc.) but some experimental errors and deviations should be accounted for. Unless indicated otherwise, parts are parts by weight, molecular weight is weight average molecular weight; temperature is in degrees Celsius; and pressure is at or near atmospheric. It should be noted that each of the Examples below represents a number of experiments which were performed with the procedures and results being summarized. It will be appreciated by those skilled in the art that not every experiment provided positive results. However, the following is believed to accurately convey the results obtained.

EXAMPLE 1

Distribution of Cationic Lipids in Normal Mice

Liposomes and/or the plasmid DNA were labeled and the cellular distribution of the labeled complexes at various times after intravenous injection were determined. The experiments were performed on pathogen-free mice (20–25 g body weight) of both sexes.

Cationic small unilamellar vesicle liposomes were prepared from the cationic lipid DDAB or DOTAP and the neutral lipid DOPE or cholesterol, labeled with Texas Red or the red fluorescent carbocyanine dye DiI or CM-DiI, and in some cases complexed to plasmid DNA containing a reporter gene such as luciferase or β-galactosidase. Endothelial cells were labeled using the fluorescent plant lectin fluorescein-*Lycopersicon esculentum*. Monocyte/macrophages were labeled by using fluorescent beads (Duke, 500 nm). Cell nuclei were labeled with DAPI, YO-PRO, or Hoechst 33342 dye.

Fluorescent liposomes or liposome-DNA complexes containing 10–60 βg of DNA in up to 300 βl were injected into unanesthetized mice via the tail vein. In some experiments, 500 nm fluorescent beads were injected after the complexes. From 5 minutes to 24 hours thereafter, the animals were anesthetized with sodium pentobarbital and then perfused through the left ventricle with fixative (1% paraformaldehyde in phosphate buffered saline) followed by the fluorescent lectin to label the endothelial surface of the vasculature. After the perfusion, tissues were removed and prepared either as whole mounts or cut into sections using a Vibratome or tissue chopper. In addition, some specimens were processed for electron microscopy. The tissues were examined by epifluorescence microscopy or by confocal microscopy. In addition, some specimens were examined by transmission electron microscopy.

Results: In mice examined from 5 minutes to 24 hours after the injection, CM-DiI or DiI-labeled liposomes or liposome-DNA complexes were most abundant in the lungs. Further, they were most numerous in endothelial cells of alveolar capillaries. The fluorescence in alveolar capillaries was uniformly distributed in all lobes of both lungs. In addition, some CM-DiI or DiI fluorescence was in intravascular monocyte/macrophages.

Next to the lung, the liver and spleen had the largest amount of labeled liposomes or complexes. In these organs, the CM-DiI or DiI fluorescence co-localized with the fluorescent beads. In the liver, the CM-DiI or DiI fluorescence and beads were in Kupffer cells. In the spleen, they were in macrophages.

The ovary also had blood vessels heavily labeled with CM-DiI or DiI-labeled liposomes or complexes. Specifically, it was observed that the endothelial cells in angiogenic blood vessels of large follicles and corpora lutea of the mouse ovary avidly took up CM-DiI or DiI-labeled DDAB:cholesterol(liposomes or)-DNA complexes after intravenous injection. These observations were documented photographically (FIG. 1). Other ovarian blood vessels contained relatively few labeled complexes. These results were used to deduce that angiogenic endothelial cells preferentially take up liposomes and liposome-DNA complexes, i.e., that the cationic liposomes used in the experiments were much more likely to associate with endothelial cell undergoing angiogenesis as compared to corresponding endothelial cells not undergoing angiogenesis.

Labeled liposomes or complexes were also very abundant in endothelial cells of high endothelial venules (HEV) of lymph nodes and Peyer's patches of the small intestine, whereas they were sparse in endothelial cells of capillaries of these lymphoid organs. Labeled liposomes or complexes were also numerous in capillary endothelial cells of the anterior pituitary, myocardium, diaphragm, adrenal cortex, and adipose tissue.

Labeled liposomes or complexes were abundant in monocyte/macrophages attached to venules of the urinary bladder, uterus, and fallopian tube. Some venules contained large numbers of labeled monocyte/macrophages. In addition, a small proportion of the endothelial cells of arterioles, capillaries, and venules in these organs were labeled.

Relatively few labeled liposomes or complexes were associated with capillary endothelial cells of the posterior pituitary, renal medulla, intestinal villi (ileum), pancreas, and adrenal medulla. Almost no labeled liposomes or complexes were found in endothelial cells in the brain, thyroid gland, renal cortex, pancreatic islets, trachea, or bronchi, with the exception of an occasional monocyte/macrophage.

Conclusions: The formulation of CM-DiI or DiI-labeled DDAB:cholesterol liposomes or liposome-DNA complexes used in these studies targeted three main cell types: endothelial cells, macrophages, and monocytes. The uptake of liposomes or complexes was organ- and vessel-specific. Most were taken up by capillary endothelial cells of the lung and macrophages of the liver and spleen. Capillary endothelial cells of the ovary, anterior pituitary, heart, diaphragm, adrenal cortex, and adipose tissue were also targeted. Blood vessels that took up liposomes or complexes in the ovary were sites of angiogenesis. In addition, HEV of lymph nodes and intestinal Peyer's patches were targeted. Targeting of endothelial cells or macrophages of other organs was less frequent and more variable. Blood vessels of the brain, thyroid, renal cortex, trachea, and bronchi were not targeted.

In addition, the experiments documented that the liposomes or complexes did not leak out of the vasculature in most organs. Although they were found in extravascular cells of the spleen, which have blood vessels with a discontinuous endothelium, they did not extravasate in other organs.

Finally, the avid uptake of cationic liposomes and liposome-DNA complexes by blood vessels of large ovarian follicles and corpora lutea indicate that the endothelial cells of angiogenic blood vessels were sites of preferential uptake.

EXAMPLE 2

Uptake of DDAB:cholesterol(liposome or)-DNA complexes in RIP-Tag5 mice

The results of the experiments of Example 1 indicated that angiogenic blood vessels in ovarian follicles and corpora lutea avidly took up cationic liposomes and liposome-DNA complexes. Accordingly, an experiment was performed to determine whether endothelial cells of angiogenic blood vessels of tumors avidly take up cationic liposomes or liposome-DNA complexes.

The transgenic RIP-tag5 model of tumors, as described under the Experimental Mouse Models Section Hanahan, D. Heritable formation of pancreatic beta-cell tumors in transgenic mice expressing recombinant insulin/simian virus 40 oncogenes. *Nature* 315: 115–22, 1985; Hanahan, D., and J. Folkman. Patterns and emerging mechanisms of the angiogenic switch during tumorigenesis. *Cell* 86: 353–64, 1996 was used. In this model, designated RIP-Tag, the oncogene from the SV-40 virus, large T antigen (Tag), is driven by a region of the rat insulin promoter (RIP). When inserted into the murine genome, this construct induces the expression of the T antigen specifically in $\beta$-cells of pancreatic islets.

One important attribute of this model is that various stages of tumor development, and therefore various stages of angiogenesis, are present concurrently in each RIP-Tag5 mouse. Although all of the 300–400 islets express the T antigen, the islets initially develop normally. However, at 6 weeks of age about half are hyperplastic, and of these, a small proportion develop into tumors by 10 weeks. Tumorigenesis appears to coincide with the onset of angiogenesis. This conversion has been designated the "angiogenic switch" Folkman, J., K. Watson, D. Ingber, and D. Hanahan, Induction of angiogenesis during the transition from hyperplasia to neoplasia, *Nature* 339: 58–61, 1989; Hanahan, D., and J. Folkman, Patterns and emerging mechanisms of the angiogenic switch during tumorigenesis. *Cell* 86: 353–64, 1996. A similar angiogenic switch appears to exist in other murine models of tumorigenesis as well as in several human tumors, Hanahan, D., and J. Folkman, Patterns and emerging mechanisms of the angiogenic switch during tumorigenesis. *Cell* 86: 353–64, 1996.

Methods and materials as per Example 1 were used. Specifically, CM-DiI or DiI-labeled DDAB:cholesterol liposomes were injected intravenously into one tumor-bearing RIP-Tag5 mouse, and CM-DiI or DiI-labeled DDAB:cholesterol-DNA complexes were injected intravenously into another RIP-Tag5 mouse. The distribution of the liposomes or complexes in angiogenic blood vessels of pancreatic islet cell tumors was examined 24 hr after the injection and was compared to that in vessels of pancreatic islets of normal mice.

Results: Two novel observations were made: (1) the liposomes or complexes were taken up by endothelial cells of angiogenic blood vessels without leaking across the endothelium, and (2) the endosomal uptake of the liposomes or complexes was greater in endothelial cells of angiogenic blood vessels than in endothelial cells of normal vessels of pancreatic islets. (FIG. 2 is of a tissue specimen).

Conclusions: This experiment gave results consistent with the preferential uptake of DDAB:cholesterol liposomes or liposome-DNA complexes by angiogenic tumor vessels. Before repeating the experiment (1) the fluorescence intensity of the liposome-DNA complexes was increased, (2) the methods of localizing sites of uptake of cationic liposomes and liposome-DNA complexes in tumors of RIP-Tag mice was improved; and (3) greater familiarity with the structure and function of angiogenic blood vessels in pancreatic islet cell tumors in RIP-Tag5 mice was obtained.

EXAMPLE 3

Uptake of DOTAP:cholesterol-DNA complexes in RIP-Tag2 mice

Purpose: The fluorescence intensity of the liposome-DNA complexes had been increased by using Texas Red-DHPE in place of DiI; the method of preparing the pancreas of RIP-Tag2 mice for localizing sites of uptake of fluorescent cationic liposome-DNA complexes was improved; and the structure and function of the angiogenic blood vessels in pancreatic islet cell tumors in RIP-Tag2 mice had been studied. With these improvements experiments of the type described in Example 2 were carried out to determine how cationic liposomes and lipid-DNA complexes were taken up.

Methods: Cationic DOTAP:cholesterol small unilamellar vesicle liposomes, labeled with Texas Red-DHPE, were prepared. Liposome-DNA complexes were prepared at a total lipid:DNA ratio of 24:1 (nmoles/$\mu$g) in 5% glucose, using 60 $\mu$g of plasmid DNA in 300 $\mu$l. Complexes (300 $\mu$l) were injected into tail veins of unanesthetized transgenic RIP1-Tag2 C57BL/6 mice and unanesthetized normal C57BL/6 mice.

Four hours after the injection of complexes, the mice were anesthetized by intraperitoneal injection of Nembutal 50 mg/kg. The vasculature was fixed by perfusion of 1% paraformaldehyde through the ascending aorta, and the luminal surface of the vasculature was stained by perfusion of green fluorescent lectin, Thurston, G., P. Baluk, A. Hirata, and D. M. McDonald, Permeability-nrelated changes revealed at endothelial cell borders in inflamed venules by lectin binding, *Am J Physiol* 271: H2547–2562, 1996. Tissue whole mounts or Vibratome sections were mounted in Vectashield, and vessels were examined using a Zeiss Axiophot fluorescence microscope or a Zeiss LSM 410 confocal microscope equipped with a krypton-argon laser and optimized photomultiplier tubes. Images were recorded on Kodak Ektachrome film (ASA 400) or as digital confocal image files.

Results: The experiment clearly showed the avid uptake of the Texas Red-labeled DOTAP:cholesterol-DNA complexes by angiogenic endothelial cells in pancreatic tumors of the RIP1-Tag2 mice. The uptake by tumor vessels far exceeded the uptake of these complexes by the corresponding endothelial cells of normal pancreatic islets (compare FIGS. 3 and 4).

The tumors were readily distinguished from adjacent tissues because of the heavy labeling of their blood vessels with the red fluorescent liposome complexes. The geometry of the vasculature of the tumors was variable, ranging from the pattern typical of normal islets to a dense, tortuous, anastomosing network of sinusoidal vessels conspicuously larger and more densely packed than in normal islets. In the latter case, the vasculature resembled that of corpora lutea. The intensity of labeling of tumor vessels was roughly related to the size of the tumor. The largest tumors had the most labeling.

Some blood vessels in small to medium size tumors had stubby, focal, aneurysm-like protrusions. These sites were particularly conspicuous because of the presence of unusually numerous Texas Red labeled dots, which were presumed to be endosomes. The Texas Red labeling of these sites was greater than that of adjacent vessels. It seemed that these structures could be capillary sprouts. The structures were not found in large tumors that had a dense, complex vasculature, where the vessels were uniformly heavily labeled.

There was no evidence of extravasation of Texas Red-labeled complexes in tumors. Also, no Texas Red-labeled complexes were seen within the clusters of extravascular erythrocytes in the tumors. The heavy labeling of the tumor vasculature resembled that of ovarian corpora lutea during the early stage of their development.

EXAMPLE 4

Uptake of cationic liposomes and liposome-DNA complexes by angiogenic blood vessels in tumors and chronic inflammation Purpose: Experiments of the type described in Example 3 were carried out to extend the observations to other models of angiogenesis. These experiments also addressed the question of whether DNA had to be present for cationic liposomes to target angiogenic blood vessels. Four animal models of angiogenesis were examined with respect to whether there was preferential uptake of DOTAP:cholesterol liposomes or liposome-DNA complexes by angiogenic blood vessels.

Models: RIP1-Tag2 tumor model. Transgenic C57BL/6 mice were produced and phenotyped at birth by PCR analysis. The mouse model is described above.

HPV tumor model. Transgenic HPV (human papilloma virus) mice were produced and phenotyped at birth by PCR analysis. Non-transgenic litter-mates were used as controls. In this model, the oncogene from the human papilloma virus is driven by a region of the keratin 14 promoter. When inserted into the murine genome, this construct induces HPV expression specifically in epidermal cells. All transgenic mice develop dysplasia accompanied by angiogenesis in the skin of the upper chest and ears, and a small proportion develop tumors.

*Mycoplasma pulmonis* infection model in mice. This infection results in chronic airway inflammation accompanied by angiogenesis in the airway mucosa. After anesthesia (87 mg/kg ketamine and 13 mg/kg xylazine injected intraperitoneally), pathogen-free, 8 week old, male and female C3H/HeNCr or C57BL/6 mice (both from Charles River) were inoculated intranasally with $3\times10^4$ colony forming units of *Mycoplasma pulmonis* (strain 5782C-UAB CT7), in a volume of 50 $\mu$l. Pathogen-free mice served as controls and were inoculated with sterile broth. Infected and control mice were caged separately under barrier conditions. Serum levels of antibody to *M. pulmonis* were measured at the end of the experiment (Microbiological Associates, Bethesda Md.). Mice were studied 1 to 8 weeks after infection.

*Mycoplasma pulmonis* infection model in rats. As in mice, this infection causes chronic airway disease, one feature of which is angiogenesis in the airway mucosa. After anesthetic (40 mg/kg ketamine and 8 mg/kg xylazine injected intraperitoneally), pathogen-free, 8 week old, male Wistar rats (from Charles River) were inoculated intranasally daily for three consecutive days with *Mycoplasma pulmonis* of the 5782C4 strain in a volume of 200 $\mu$l. Pathogen-free rats inoculated with broth served as controls. Infected and control rats were caged separately under barrier conditions. Serum levels of antibody to *M. pulmonis* and other pathogens were measured at the end of the experiment (Microbiological Associates, Bethesda Md.).

Methods: Cationic DOTAP:cholesterol liposomes, labeled with Texas Red-DHPE, were prepared as described under Example 3. Liposomes were injected into a tail vein of mice at a dose of 360 nmol total lipid in a volume of 100 μl in 5% glucose. Rats were infected via the femoral vein. Liposome-DNA complexes were prepared at a total lipid:DNA ratio of 24:1 in 5% glucose, using 60 μg of plasmid DNA in 200–300 μl. Liposomes or complexes (200–300 μl) were injected into a tail vein of unanesthetized RIP-Tag2, HPV, or *M. pulmonis*-infected mice. Non-transgenic, pathogen-free mice were used as controls.

At 20 minutes or 4 hours after the injection, the mice or rats were anesthetized by intraperitoneal injection of Nembutal 50 mg/kg. The vasculature was fixed by perfusion of 1% paraformaldehyde through the ascending aorta, and the luminal surface of the vasculature was stained by perfusion of green fluorescent lectin, Thurston, G., P. Baluk, A. Hirata, and D. M. McDonald. Permeability-related changes revealed at endothelial cell borders in inflamed venules by lectin binding. Am J Physiol 271: H2547–2562, 1996. Tissue whole mounts or Vibratome sections were mounted in Vectashield, and vessels were examined with a Zeiss fluorescence microscope or confocal microscope.

The amount of uptake of fluorescent liposomes or complexes was quantified by confocal microscopy. Briefly, a series of 12 confocal images separated by 2.5 μm in the focal (z) axis was collected in the rostral region of the trachea in the fluorescein and Texas Red channels using a 20× NA 0.6 lens (Zeiss) and standardized settings of the confocal pinhole size, photomultiplier tube gain, and laser power. Projections were generated from the image series showing the vessels (fluorescein-*L. esculentum*) and liposomes (Texas Red) separately. Using the confocal software, regions approximately 200 μm² in area were defined on the vessel images, then the average fluorescence of the corresponding regions of the liposome image was measured. Background intensity was determined by measuring fluorescence in selected regions adjacent to the vessels. Measurements were made on 25 vessels per trachea and 4 tracheas per group (n=4). The significance of differences was assessed by Student's t test.

Tissues prepared for transmission electron microscopy were processed as described previously, McDonald, D. M. Endothelial gaps and permeability of venules of rat tracheas exposed to inflammatory stimuli, *Am. J. Physiol.* 266: L61–L83, 1994. Briefly, perfusion of primary fixative (3% glutaraldehyde in 75 mM cacodylate buffer, pH 7.1, plus 1% sucrose, 4% PVP, 0.05% CaCl2, and 0.075% H2O2) for 5 min at room temperature was followed by perfusion of secondary fixative (3% glutaraldehyde in cacodylate buffer 75 mM, pH 7.1, containing 0.05% CaCl2, 1% sucrose, and 4% PVP) for 5 min. Tissues were left to fix in situ for 1 hr at room temperature then removed and left overnight in secondary fixative at 4° C. Tissues were trimmed with a razor blade or sliced with a tissue chopper, post-fixed in osmium (2% OsO4 in 100 mM cacodylate buffer, pH 7.4, for 18 hr at 4° C.), washed in H₂O (18 hr at 4° C.), and stained en bloc with uranyl acetate (aqueous, 37° C. for 48 hrs). Tissue was then dehydrated through acetone, infiltrated, and embedded in epoxy resin. Ultra-thin sections were cut with an ultramicrotome, mounted on single-slot specimen grids, and examined with a Zeiss EM-10 electron microscope.

Results: The experiments revealed that Texas Red-labeled DOTAP:cholesterol liposomes, in the absence of DNA, selectively targeted angiogenic endothelial cells of tumors in RIP1-Tag2 mice, similar to previous findings with Texas Red-labeled DOTAP:cholesterol-DNA complexes and DiI-labeled DDAB:cholesterol-DNA complexes. This and subsequent experiments on transgenic RIP1-Tag2 mice confirmed that the uptake of cationic liposomes by angiogenic blood vessels of hyperplastic islets and tumors far exceeded that of the corresponding normal vessels (FIGS. 5, 6, 7 and 8). In some vessels of hyperplastic islets and small tumors, liposomes were taken up by endothelial cells only in focal regions (FIG. 8), whereas in larger tumors the uptake was more generalized (FIG. 6). Focal regions of uptake were thought to be possible sites of new vessel growth (FIG. 8).

Because this property of cationic liposomes or liposome-DNA complexes had the potential practical use of selectively delivering substances to angiogenic endothelial cells, it seemed desirable to determine whether this property of angiogenic endothelial cells in tumors was shared by endothelial cells at other sites of pathological angiogenesis. This question was addressed in experiments where the uptake of Texas Red-labeled DOTAP:cholesterol liposomes by angiogenic endothelial cells was examined in the trachea of mice with *Mycoplasma pulmonis* infection, which causes chronic airway inflammation, one feature of which is angiogenesis (compare FIGS. 9 and 10). Angiogenic endothelial cells in regions of chronic inflammation were found to be sites of unusually high uptake of cationic liposomes (FIG. 10). Specifically, vessels in the tracheas of mice infected with *M. pulmonis* had an unusually large amount of uptake. Confocal microscopic measurements of angiogenic blood vessels showed that the infected mice had 20- to 30-fold more uptake than controls (FIG. 11). Some angiogenic vessels had 100 times as much uptake. Confocal- and electron microscopic studies of angiogenic endothelial cells in mice infected with *M. pulmonis* suggested that cationic liposomes first associated with (FIG. 12) and were then internalized into endosomes (FIGS. 13).

Similarly, cationic liposomes were avidly taken up by angiogenic blood vessels in ovarian follicles and corpora lutea in mice, dysplastic skin of transgenic HPV mice, and tracheas of rats with angiogenesis due to *M. pulmonis* infection.

Conclusions: These experiments confirmed that cationic liposomes and liposome-DNA complexes preferentially target the angiogenic endothelial cells of tumors and sites of chronic inflammation.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

BIBLIOGRAPHY

The following documents are cited by letter and number throughout the text supra. Their contents are hereby expressly incorporated by reference herein:

A. U.S. Pat. No. 4,897,355
B. U.S. Pat. No. 4,394,448
C. U.S. Pat. No. 5,328,470
D. WO93/12240
E. WO/91/06309
F. Huang, et al, Cancer Res. 52, 5135 (1992).
G. Rosenecker et al., PNAS 93, 7236 (1996).
H. Abdi, et al., In Vitro Cell Dev. Biol. Anim. 31, 310 (1995).
I. Chonn et al., Curr. Opin. Biotechnol. 6, 698 (1995).

J. Green, et al., Adv. Exp. Med. Biol. 383, 83 (1995).

K. Hung, et al, Gene 159, 65 (1995).

L. Ledley, et al., Hum. Gene Ther. 6, 1129 (1995).

M. Mori, et al., Cancer Chemother. Pharmacol. 35, 447 (1995).

N. Volm, et al.,et al, Curr. Opin. Oncol. 7, 429 (1995).

O. Litzinger, et al., Biochim. Biophys. Acta 1190, 99 (1994).

P. Northfelt, et al., Drugs 48, 569 (1994).

Q. Oku, et al., Crit. Rev. Ther. Drug Carrier Sys. 11, 231 (1994).

R. Gabizon, et al., Ann Biol.Clin (Paris) 51, 811 (1993).

S. Huang, et al, Am. J. Pathol. 143, 10 (1994).

T. Mori, et al., Pharm. Res. 10, 507 (1993).

U. Priebe, et al., Pharmacol. Ther. 60, 215 (1993).

V. Straubinger, et al., J. Natl. Cancer Inst. Monogr. 69 (1993).

W. Fidler, et al., World J. Surg. 16, 270 (1992).

X. Rowlinson-Busza, et al., Curr. Opin. Oncol. 4, 1142 (1992).

Y. Sugarman, et al., Crit. Rev. Oncol. Hematol. 12, 231 (1992).

Z. Pak, et al., Biotherapy 3, 55 (1991).

AA. De Smidt, et al., Crit. Rev. Ther. Drug Carrier Syst. 7, 99 (1990).

BB. Papahadjopoulos, et al., Prog. Clin. Biol. Res. 343, 85 (1990).

CC. Shibata, et al., Neurol. Med. Chir. (Tokyo) 30, 242 (1990).

DD. Hughes, et al., Cancer Res. 49, 6214 (1989).

EE. Shibata, et al., Neurol. Med. Chir. (Tokyo) 29, 696 (1989).

FF. Freeman, et al., Cancer 58, 573 (1986).

GG. Zolotareva, et al., Eksp. Onkol. 8, 28 (1986).

HH. Caride, et al., Crit. Rev. Ther. Drug Carrier Syst. 1, 121 (1985).

II. Yatvin, et al., Med. Phys. 9, 149 (1982).

JJ. Liposomes, A Practical Approach, edited by Nev, R.R.C., IRL Press, 1994.

KK. Liposomes, From Physics to Applications, Lasic, D. D., Elsevier, 1993.

Literature cited in Examples:

1. Arfors, K. -E., G. Rutili, and E. SvensjÜ. Microvascular transport of macromolecules in normal and inflammatory conditions. Acta Physiol. Scand. Suppl. 463: 93–103, 1979.

2. Baluk, P., and D. M. McDonald. The b2-adrenergic receptor agonist formoterol reduces microvascular leakage by inhibiting endothelial gap formation. Am. J. Physiol. 266: L461–L468, 1994.

3. Bowden, J. J., A. Garland, P. Baluk, P. Lefevre, E. Grady, S. R. Vigna, N. W. Bunnett, and D. M. McDonald. Direct observation of substance P-induced internalization of neurokinin 1 (NK1) receptors at sites of inflammation. Proc. Natl. Acad. Sci. USA 91: 8964–8968, 1994.

4. Brigham, K., B. Meyrick, B. Christman, M. Magnuson, G. King, and L. C. Berry. In vivo transfection of murine lungs with a functioning prokaryotic gene using a liposome vehicle. Am. J. Med. Sci. 298: 278–281, 1989.

5. Christenson, L. K., and R. L. Stouffer. Proliferation of microvascular endothelial cells in the primate corpus luteum during the menstrual cycle and simulated early pregnancy. Endocrinology 137: 367–374, 1996.

6. Conary, J. T., R. E. Parker, B. W. Christman, R. D. Faulks, G. A. King, B. O. Meyrick, and K. L. Brigham. Protection of rabbit lungs from endotoxin injury by in vivo hyperexpression of the prostaglandin G/H synthase gene. J. Clin. Invest. 93: 1834–1840, 1994.

7. Folkman, J., K. Watson, D. Ingber, and D. Hanahan. Induction of angiogenesis during the transition from hyperplasia to neoplasia. Nature 339: 58–61, 1989.

8. Hanahan, D. Heritable formation of pancreatic beta-cell tumors in transgenic mice expressing recombinant insulin/simian virus 40 oncogenes. Nature 315: 115–22, 1985.

9. Hanahan, D., and J. Folkman. Patterns and emerging mechanisms of the angiogenic switch during tumorigenesis. Cell 86: 353–64, 1996.

10. Lundberg, J. M., and A. Saria. Capsaicin-induced desensitization of airway mucosa to cigarette smoke, mechanical and chemical irritants. Nature 302: 251–253, 1983.

11. Majno, G., and G. E. Palade. Studies on inflammation. I. The effect of histamine and serotonin on vascular permeability: an electron microscopic study. J. Biophys. Biochem. Cytol. 11: 571–604, 1961.

12. McDonald, D. M. Neurogenic inflammation in the rat trachea. I. Changes in venules, leucocytes, and epithelial cells. J. Neurocytology 17: 583–603, 1988.

13. McDonald, D. M. The ultrastructure and permeability of tracheobronchial blood vessels in health and disease. Eur. J. Respir. Dis. 3 (Suppl 12): 572s–585s, 1990.

14. McDonald, D. M. Endothelial gaps and permeability of venules of rat tracheas exposed to inflammatory stimuli. Am. J. Physiol. 266: L61–L83, 1994.

15. McDonald, D. M., and A. Goldfein. The relation of lutein cell Golgi apparatus morphology to ovarian progesterone secretion during the rat estrous cycle. Anat. Rec. 151: 385, 1965.

16. McDonald, D. M., K. Seiki, M. Prizant, and A. Goldfein. Ovarian progesterone secretion in relation to the lutein cell Golgi apparatus during rat estrous cycle. Endocrinology 85: 236–243, 1969.

17. Nabel, E. G., D. Gordon, Z. Y. Yang, L. Xu, H. San, G. E. Plautz, B. Y. Wu, X. Gao, L. Huang, and G. J. Nabel. Gene transfer in vivo with DNA-liposome complexes: lack of autoimmunity and gonadal localization. Hum. Gene Ther. 3: 649–56, 1992.

18. Philip, R., D. Liggitt, M. Philip, P. Dazin, and R. J. Debs. In vivo gene delivery: Efficient transfection of T lymphocytes in adult mice. J. Biol. Chem. 268: 16087, 1993.

19. Thurston, G., P. Baluk, A. Hirata, and D. M. McDonald. Permeability-related changes revealed at endothelial cell borders in inflamed venules by lectin binding. Am J Physiol 271: H2547–2562, 1996.

20. Tsukada, K., T. Matsushima, and N. Yamanaka. Neovascularization of the corpus luteum of rats during the estrus cycle. Pathol Int 46: 408–416, 1996.

21. Umeno, E., J. A. Nadel, and D. M. McDonald. Neurogenic inflammation of the rat trachea: fate of neutrophils that adhere to venules. J. Appl. Physiol. 69: 2131–2136, 1990.

22. Zhu, N., D. Liggitt, Y. Liu, and R. Debs. Systemic gene expression after intravenous DNA delivery into adult mice. Science 261: 209–211, 1993.

23. Bowden, J. J., T. R. Schoeb, J. R. Lindsey, and D. M. McDonald. Dexamethasone and oxytetracycline reverse the potentiation of neurogenic inflammation in airways of rats with *Mycoplasma pulmonis* infection. Am J Respir Crit Care Med 150: 1391–401, 1994.

24. McDonald, D. M. Infections intensify neurogenic plasma extravasation in the airway mucosa. Am Rev Respir Dis 146: S40–4, 1992.

25. McDonald, D. M. Upregulation of tachykinin receptors in an animal model of chronic airway inflammation. Pulmonary Pharmacology 8: 203–205, 1995.

26. McDonald, D. M., T. R. Schoeb, and J. R. Lindsey. *Mycoplasma pulmonis* infections cause long-lasting potentiation of neurogenic inflammation in the respiratory tract of the rat. J Clin Invest 87: 787–99, 1991.

What is claimed is:

1. A method of selectively affecting angiogenic endothelial cells in vivo, comprising the steps of:
    administering to a mammal a liposomal composition comprising cationic lipids and a substance that affects angiogenesis which substance is selected from the group consisting of angiogenic enhancers and angiogenic inhibitors wherein the liposomal composition has greater affinity for angiogenic endothelial cells as compared to corresponding normal endothelial cells; and
    allowing the liposomal composition to selectively associate with angiogenic endothelial cells of an angiogenic blood vessel for a time and in a manner such that the liposomal composition enters the angiogenic endothelial cells.

2. The method of claim 1, wherein the liposomal composition is administered by injection into the circulatory system of the mammal and further wherein the liposomal composition has five-fold or greater affinity for angiogenic endothelial cells as compared to corresponding normal endothelial cells.

3. The method of claim 2, wherein the injected liposomal composition has ten-fold or greater affinity for angiogenic endothelial cells as compared to corresponding normal endothelial cells and further wherein the liposomal composition is comprised of 5 mole % or more cationic lipids and the liposomal composition is injected intraarterially.

4. The method of claim 1, wherein the substance which affects angiogenesis is an inhibitor of angiogenesis.

5. The method of claim 1, wherein the substance which affects angiogenesis is a promoter of angiogenesis.

6. The method of claim 1, wherein the substance that affects angiogenesis is a nucleotide sequence that expresses a protein that affects angiogenesis.

7. The method of claim 1, wherein the substance that affects angiogenesis is an antisense RNA sequence which disrupts the expression of DNA being expressed within an angiogenic endothelial cell.

8. The method of claim 6, wherein said nucleotide sequence which encodes a protein is operatively attached to a promoter sequence.

9. The method of claim 8, wherein the promoter is activated, selectively, within an angiogenic endothelial cell and not activated in a corresponding quiescent endothelial cell.

10. The method of claim 9, wherein the protein promotes a thrombogenic cascade.

11. A method of reducing the blood supply, in vivo, to a site of angiogenesis, comprising the steps of:
    administering to a patient with a site of angiogenesis liposomal DNA/cationic lipid complexes wherein the complexes have greater affinity for angiogenic endothelial cells as compared to corresponding normal endothelial cells, the liposomal complexes comprising DNA which encodes a protein which inhibits angiogenesis wherein the complexes are administered by injection into the circulatory system such that the amount of protein expressed by the DNA is sufficient to kill angiogenic endothelial cells in blood vessels of the site of angiogenesis; and
    allowing the liposomal complexes to associate with and enter angiogenic endothelial cells of angiogenic blood vessels leading to the site of angiogenesis where the protein which inhibits angiogenesis terminates a sufficient number of the endothelial cells so as to substantially reduce the blood supply to the site of angiogenesis.

12. A method of diagnosing a site of angiogenesis, in vivo, comprising:
    administering liposomal complexes comprising cationic lipids and a detectable label wherein the complexes have greater affinity for angiogenic endothelial cells as compared to corresponding normal endothelial cells;
    allowing the liposomal complexes to selectively associate with angiogenic endothelial cells; and
    detecting the label and thereby determining a site of angiogenesis based on an accumulation of the label at the site.

13. The method of claim 12, wherein the detectable label is selected from the group consisting of fluorescent labels histochemical labels, immunohistochemical labels and radioactive labels, the method further comprising:
    isolating tissue at the site of label accumulation; and
    analyzing the isolated tissue.

* * * * *